United States Patent [19]

Janssens et al.

[11] 4,219,559

[45] Aug. 26, 1980

[54] N-HETEROCYCLYL-4-PIPERIDINAMINES

[75] Inventors: Frans Janssens, Rijmenam; Raymond Stokbroekx; Joseph Torremans, both of Beerse; Marcel Luyckx, Geel, all of Belgium

[73] Assignee: Janssen Pharmaceutica N.V., Beerse, Belgium

[21] Appl. No.: 2,276

[22] Filed: Jan. 10, 1979

Related U.S. Application Data

[63] Continuation-in-part of Ser. No. 892,534, Apr. 3, 1978, abandoned.

[51] Int. Cl.$^2$ .................. A61K 31/445; C07D 401/04
[52] U.S. Cl. .................................... 424/267; 424/256; 424/263; 424/248.51; 424/248.54; 424/248.55; 424/248.56; 546/118; 546/194; 546/199; 544/127; 544/139

[58] Field of Search ........................ 546/118, 194, 199; 544/127, 139; 424/248.51, 248.54, 248.55, 248.56, 256, 263, 267

[56] References Cited

U.S. PATENT DOCUMENTS

| | | | |
|---|---|---|---|
| 3,963,727 | 6/1976 | Ueno et al. | 546/199 |
| 3,989,707 | 11/1976 | Janssen et al. | 546/199 |
| 4,002,623 | 1/1977 | Kadin | 546/199 |

*Primary Examiner*—John M. Ford
*Assistant Examiner*—Robert T. Bond
*Attorney, Agent, or Firm*—Geoffrey G. Dellenbaugh

[57] ABSTRACT

Novel N-heterocyclyl-4-piperidinamines wherein said heterocyclic radical is an optionally substituted 1H-benzimidazol-2-yl or 3H-imidazo[4,5-b]pyridin-2-yl radical, said compounds being useful as antihistaminic agents.

19 Claims, No Drawings

N-HETEROCYCLYL-4-PIPERIDINAMINES

CROSS-REFERENCE TO RELATED APPLICATIONS:

This is a continuation-in-part of our copending application Ser. No. 892,534, filed Apr. 3, 1978, now abandoned.

BACKGROUND OF THE INVENTION

In U.S. Pat. No. 2,971,005 there are described 2-(phenylmethylamino)benzimidazoles having local anaesthetic and antifibrillatory properties and in U.S. Pat. No. 2,857,391 there are described a number of 2-(aminomethyl)benzimidazoles. The compounds of this invention differ therefrom essentially by the nature of the 4-piperidinyl-group, attached to the amino nitrogen atom and by their unexpected antihistaminic properties. Also known in the art is 1-methyl-N-phenyl-N-phenylmethyl-4-piperidinamine, an antihistaminic compound which is generically designated as Bamipine (see the Merck index, 8th edition (1968) p. 118). The compounds of this invention are structurally different since they invariably contain a 1H-benzimidazol-2-yl or 3H-imidazo [4,5-b]pyridin-2-yl radical, attached to the amino nitrogen atom.

DESCRIPTION OF THE PREFERRED EMBODIMENTS:

This invention is concerned with a novel series of N-heterocyclyl-4-piperidinamines which may structurally be represented by the formula:

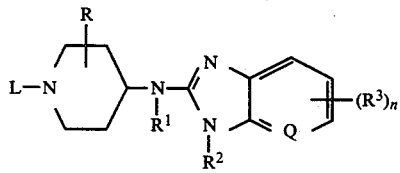
(I)

and the pharmaceutically acceptable acid addition salts thereof, wherein

R is a member selected from the group consisting of hydrogen and lower alkyl;

$R^1$ is a member selected from the group consisting of hydrogen, lower alkyl, cycloalkyl, aryllower alkyl and lower alkanoyl;

$R^2$ is a member selected from the group consisting of hydrogen, alkyl having from 1 to 10 carbon atoms, aryl, cycloalkyl and mono-and diaryl(lower alkyl);

$R^3$ is a member independently selected from the group consisting of halo, lower alkyl, lower alkyloxy and trifluoromethyl;

n is an integer of from 0 to 2 inclusive;

Q is a member selected from the group consisting of CH and N; and

L is a member selected from the group consisting of lower alkyl, which is optionally substituted with up to 3 substituents each independently selected from the group consisting of halo, cyano, hydroxy, isothiocyanato, lower alkyloxy, aryl, aryloxy, arylthio, arylsulfonyl, amino; lower alkenyl; aryllower alkenyl; cycloalkyl, being optionally substituted with a cyano and/or an aryl group; 1-(aryllower alkyl)-1H-benzimidazol-2-yl; and a radical of the formula $Z-C_mH_{2m}-$, wherein m is an integer of from 1 to 6 inclusive; and Z is a member selected from the group consisting of 4,5-dihydro-5-oxo-1H-tetrazol-1-yl, being optionally substituted in its 4-position by an aryl radical or a lower alkyl radical; 2,3-dihydro-1,4-benzodioxin-2-yl; 2,3-dihydro-1,4-benzodioxin-6-yl; 2,3-dihydro-2-oxo-1H-benzimidazol-1-yl; 2,3-dihydro-3-oxo-4H-benzoxazin-4-yl; (10,11-dihydro-5H-di-benzo[a,d]cyclohepten-5-ylidene)methyl; 4-morpholinyl; 1-piperidinyl; 1-pyrrolidinyl; a radical of the formula T-$N(R^4)-$, wherein $R^4$ is a member selected from the group consisting of hydrogen, lower alkyl and aryllower alkyl; and T is a member selected from the group consisting of lower alkyl, aryl, aryllower alkyl, 1H-benzimidazol-2-yl; and a radical of the formula

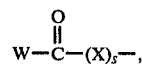

wherein s is the integer 0 or 1;

X is a member selected from the group consisting of 0 and $-N(R^5)-$, said $R^5$ being a member selected from the group consisting of hydrogen, lower alkyl, aryllower alkyl, lower alkanoyl and aroyl; and W is a member selected from the group consisting of lower alkyl, aryl, aryllower alkyl, amino, arylamino, mono- and di(lower alkyl)amino, mono- and di(aryllower alkyl)amino, 1-piperidinyl, 1-pyrrolidinyl and 4-morpholinyl;

wherein aryl as used in the foregoing definitions, is a member selected from the group consisting of phenyl, substituted phenyl, naphthalenyl, thienyl, halothienyl, (lower alkyl)thienyl, pyridinyl, mono-and di(lower alkyloxy)pyridinyl, furanyl and 1-(lower alkyl)pyrrolyl; wherein said substituted phenyl is phenyl having from 1 to 3 substitutents each independently selected from the group consisting of halo, hydroxy, nitro, cyano, trifluoromethyl, lower alkyl, lower alkylthio, lower alkylsulfonyl, lower alkylsulfonyllower alkyl, phenyllower alkylsulfonyl, phenylsulfonyllower alkyl, amino, mono- and di(lower alkyl)amino, lower alkanoyl, a radical of the formula $R^6-C_pH_{2p}-O-$, wherein p is an integer of from 1 to 6 inclusive; and $R^6$ is a member selected from the group consisting of hydrogen, amino, cyano, phenyl, aminocarbonyl, mono- and di(lower alkyl)aminocarbonyl, lower alkyloxycarbonyl, phenyllower alkyloxycarbonyl, 4-morpholinylcarbonyl, 1-piperidinylcarbonyl and 1-pyrrolidinylcarbonyl, lower alkenyl; and a radical of the formula $R^7-O-$, wherein $R^7$ is a member selected from the group consisting of alkanoyl, phenylcarbonyl, phenyllower alkylcarbonyl, lower alkyloxycarbonyl, phenyllower alkyloxycarbonyl, aminocarbonyl, phenylaminocarbonyl, mono- and di(lower alkyl)aminocarbonyl;

wherein said phenyl in the definition of said $R^7$ may be optionally substituted with up to 3 substituents each independently selected from the group consisting of halo, cyano, nitro, lower alkyl and lower alkyloxy; and wherein said aroyl in the definition of said L represents arylcarbonyl wherein said aryl is as defined hereabove.

As used in the foregoing definitions the term "lower alkyl" is meant to include straight and branch chained hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; the term "alkyl" as used in the definition of $R^2$ includes straight and branch chained hydrocarbon radicals having from 1 to 10 carbon atoms, such as, for example, the above-indicated lower alkyls and higher homologs such as heptyl, octyl, nonyl and decyl; the term "lower alkenyl" refers to straight alkenyl radicals having from 3 to 6 carbon atoms wherein the unsaturation is preferably located at the $\beta$-position but may also be located at the $\gamma$, $\delta$, or $\epsilon$-position such as for example, 2-propenyl, 2-butenyl, 3-pentenyl, 2-hexenyl and the like; the term "cycloalkyl" refers to cyclic hydrocarbon radicals having from 3 to 6 carbon atoms such as cyclopropyl, cyclobutyl, cyclopentyl and cyclohexyl, and the term "halo" is generic to fluoro, chloro, bromo and iodo.

The compounds of formula (I) can generally be derived from a starting material of the formula

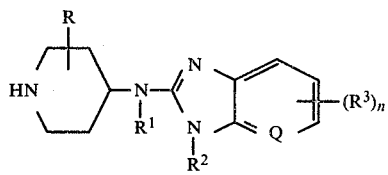

wherein R, $R^1$, $R^2$, $R^3$, n and Q are as previously defined by introducing the desired L-substituent onto the piperidine nitrogen by the application of art-known methods.

In general the introduction of said L into the intermediate (II) may conveniently be accomplished by the reaction of (II) with an appropriate reactive ester of the formula LY, (III), wherein L is as previously defined and Y is a reactive ester residue such as, for example, halo, preferably chloro or bromo, or a sulfonyloxy residue such as, for example, methylsulfonyloxy or 4-methylphenylsulfonyloxy and the like. The condensation reaction of (II) with (III) is conveniently conducted in an inert organic solvent such as, for example, an aromatic hydrocarbon, e.g., benzene, methylbenzene, dimethylbenzene, and the like; a lower alkanol, e.g., methanol, ethanol, 1-butanol and the like; a ketone, e.g., 4-methyl-2-pentanone and the like; an ether, e.g., 1,4-dioxane, 1,1'-oxybisethane and the like; N,N-dimethylformamide (DMF); nitrobenzene; and the like.

The additon of an appropriate base such as, for example, an alkali metal carbonate or hydrogen carbonate, or an organic base such as, for example N,N-diethylethanamine or N-(1-methylethyl)-2-propanamine may be utilized to pick up the acid that is liberated during the course of the reaction. In some circumstances the addition of an iodide salt, preferably an alkali metal iodide, is appropriate. Somewhat elevated temperatures may be employed to enhance the rate of the reaction.

When L in formula (I) represents a(2,3-dihydro-2-oxo-1H-benzimidazol-1-yl) lower alkyl radical it is appropriate to use a reactive ester (III) wherein the nitrogen atom in the 3-position of the of the 2,3-dihydro-2-oxo-1H-benzimidazol-1-yl group is substituted with an appropriate protecting group, preferably a 1-methylethenyl group and removing said protecting group after completion of the condensation reaction. The removal of said protecting group may be accomplished by art-known procedures, such as acid hydrolysis when a 1-methylethenyl group is involved.

When L represents a 2-aryl-2-hydroxyethyl or a 3-aryloxy 2-hydroxypropyl radical, the introduction of said substituent into the intermediate (II) may conveniently be carried out by reacting (II) at an elevated temperature with an appropriate oxirane of the formula

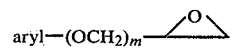 (IV)

wherein m is 0 or 1.

The reaction of (II) with (IV) may be carried out in an appropriate organic solvent or, optionally, in the absence of any solvent. Suitable solvents which may be employed include, for example, aromatic hydrocarbons such as benzene, methylbenzene, dimethylbenzene and the like; halogenated hydrocarbons such as, for example, trichloromethane, dichloromethane and the like; lower alkanols such as, methanol, ethanol, 2-propanol and the like alcohols; and mixtures of such solvents. When the piperidine derivative (II) is in the form of an acid addition salt it is appropriate to add to the reaction mixture an appropriate base such as, for example, sodium carbonate in order to liberate the free acid from the salt.

The compounds of formula (I) wherein L represents a 2-hydroxyethyl radical may be prepared by the reaction of an appropriate piperidine of formula (II) with oxirane, following the same procedure as described for the reaction of (IV) with (II).

When L is, at the point of attachment to the piperidine nitrogen atom, a primary or secondary alkyl group, the compounds (I) may also be prepared by the reductive amination of an aldehyde or ketone corresponding with the alcohol L—OH with a piperidine derivative of formula (II) following art-known procedures. In a convenient method of operation a mixture of the aldehyde or ketone and (II) in an appropriate organic solvent is hydrogenated in the presence of an appropriate catalyst such as, for example, palladium-on-charcoal.

Appropriate organic solvents include lower alkanols, such as, for example, methanol, ethanol, propanol and the like. The rate of the hydrogenation reaction may be enhanced by carrying out said reaction in the presence of an appropriate weak acid such as, for example, acetic acid. When the piperidine derivative (II) is in the form of an addition salt with a strong acid, e.g., hydrochloric or hydrobromic acid it is appropriate to add thereto a salt of a strong base with a weak acid., e.g., sodium acetate to bind said strong acid. When (II) contains groups that are themselves susceptable to catalytic hydrogenation, e.g. when $R^2$ represents a arylmethyl group, it may be appropriate to add to the reaction mixture an appropriate catalyst poison, such as, for example, thiophene.

When L represents a radical of formula Z—$C_mH_{2m}$—, wherein m is an integer of from 2 to 6 inclusive and wherein Z is as previously defined, the compounds of formula (I) can also be prepared by the reaction of (II) with an appropriate alkenyl derivative, Z—$C_mH_{2m-1}$, according to art-known methods of carrying out similar addition- reactions, e.g., by stirring and heating the reactants together in and appropriate reaction-inert organic solvent such as, for example, a lower alkanol such as 2-propanol, butanol and the like.

When L represents a 2-(aroylamino)ethyl radical or a 2-arylethyl radical the compounds (I) can also be obtained by the reaction of (II) with an appropriate I-aroylaziridine or an appropriate ethenylarene, respectively. Said reactions are preferably carried out in an appropriate reaction-inert organic solvent, such as, for example, a lower alkanol, e.g. methanol, ethanol, propanol, butanol and the like alcohols; an aromatic hydrocarbon, e.g., benzene, methylbenzene, dimethylbenzene and the like; a ketone, e.g., 4-methyl-2-pentanone; an ether, e.g., 1,4-dioxane, 1,1'-oxybisethane and the like; N,N-dimethylformamide; nitrobenzene; and the like; or a mixture of such solvents. Elevated temperatures are appropriate in order to enhance the rate of the reaction and preferably the reaction is carried out at the reflux temperature of the reaction mixture.

The compounds of formula (I) can also be prepared by the cyclodesulfurization of an appropriate thiourea derivative of the formula

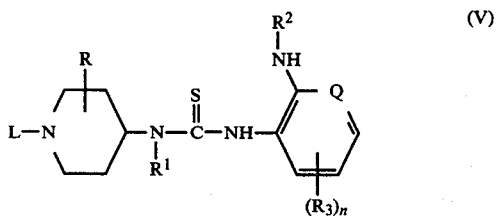

(V)

Said cyclodesulfurization reaction may be carried out by the reaction of (V) with an appropriate alkyl halide, preferably iodomethane in an appropriate reaction-inert organic solvent, e.g., a lower alkanol such as methanol, ethanol, 2-propanol and the like. Otherwise, the cyclodesulfurization reaction may be carried out by the reaction of (V) with an appropriate metal oxide or salt in an appropriate solvent according to the procedure described, for example, in Pharmazie, 31, 348 (1976). For example, the compounds of formula (I) can easily be prepared by the reaction of (V) with an appropriate Hg(II) or Pb(II) oxide or salt, such as, for example HgO, $HgCl_2$, $Hg(OAc)_2$, PbO or $Pb(OAc)_2$. In certain instances it may be appropriate to supplement the reaction mixture with a small amount of sulfur. Even so methanediimines, especially N,N'-methanetetraylbis[cyclohexanamine], may be used as cyclodesulfurizing agents. Suitable reaction-inert organic solvents that may advantageously be employed include lower alkanols, e.g., methanol, ethanol, 2-propanol and the like; halogenated hydrocarbons, e.g., dichloromethane and trichloromethane; ethers, e.g. tetrahydrofuran, 2,2'-oxybispropane and the like; and mixture of such solvents.

The compounds of formula (I) wherein $R^2$ is other than hydrogen, said $R^2$ being represented by $R^2$ and said compounds by the formula (I-a), can also be prepared starting from a corresponding compound (I) wherein $R^2$ is hydrogen, (I-b), by introducing said $R^2$ according to art-known procedures as previously described herein for the introduction of L into starting materials of formula (II). In a preferred method of operation (I-b) is reacted with an appropriate reactive ester $R^2$ Y, (VI), wherein $R^2$ and Y are as previously defined. The reaction is carried out under similar conditions as previously described herein for the reaction of (II) with (III). Since the compounds of formula (I-b) are somewhat less reactive it is advantageous to conduct the alkylation reaction in the presence of a small amount of a strong metal base such as, for example, sodium hydride.

The compounds of formula (I) wherein $R^1$ and $R^2$ are both different from hydrogen, said $R^1$ being represented by $R^1$ and said $R^2$ by $R^2_a$ can also be derived from the corresponding compounds wherein $R^1$ is hydrogen by introducing the $R^1_a$-group in a similar manner as described hereinabove for the preparation of compound (I-b) starting from (I-a).

Following the procedure, described hereinabove for the preparation of compounds (I) starting from (V), the compounds of formula (I), wherein L represents a (1H-benzimidazol-2-ylamino)lower alkyl radical or a 1-(aryllower alkyl)-1H-benzimidazol-2-ylamino)lower alkyl radical (I-c), may even so be derived from the corresponding isothiocyanates (VII) by subjecting the latter to an addition-reaction with a benzenediamine (VIII) and subsequently cyclodesulfurizing the intermediately formed thiourea (IX).

The isothiocyanates (VII) may be prepared following art-known procedures for the preparation of isothiocyanates [see, for example, Saul Patal Ed. "The Chemistry of Cyanates and their Thioderivatives" John Wiley & Sons—Chichester—New York—Brisbane—Toronto (1977) p. 1013–1053], such as, for example by reacting the corresponding amine (VI) with carbon disulfide, preferably in the presence of alkali e.g., sodium hydroxide and the like, and decomposing the intermediately formed dithiocarbamate with for example N,N'-methanetetraylbis[cyclohexanamine], a lower alkyl chloroformate or another appropriate decomposing agent as known in the art.

The foregoing reactions are illustrated as follows:

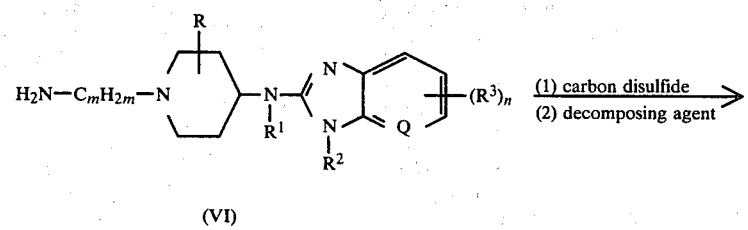

(VI)

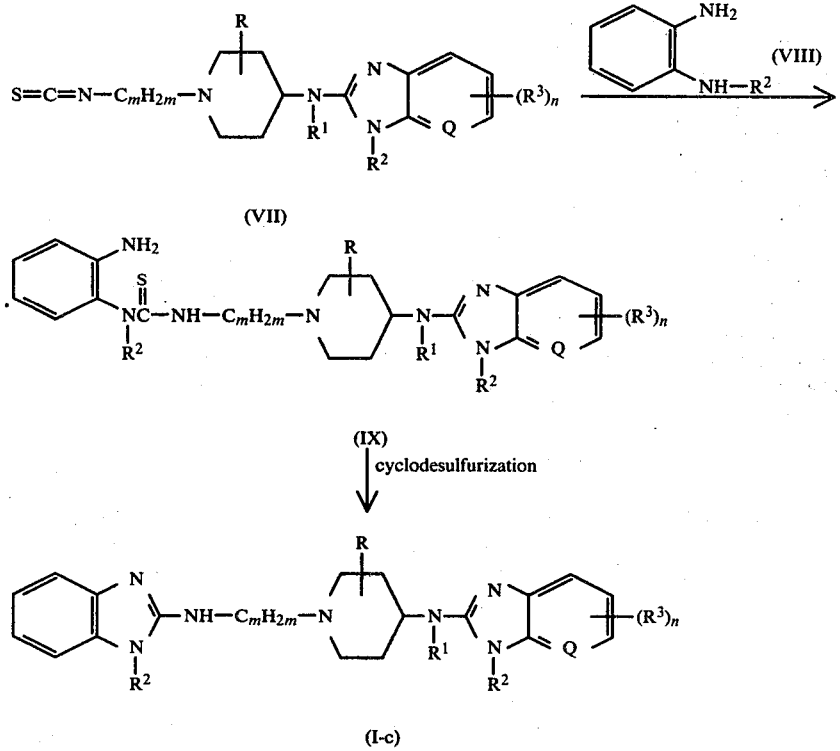

(I-c)

The compounds of formula (I) wherein L represents a radical Z—$C_mH_{2m}$—, wherein Z represents a radical of the formula W—CO—$(X)_s$—, wherein s is 1, X is O and W is an optionally substituted amine, a 1-pyrrolidinyl, a 4-morpholinyl or a 1-piperidinyl radical, said compounds being represented by the formula (I-d), may be prepared by the reaction of the corresponding amine, pyrrolidine, morpholine or piperidine with an appropriate N-[1-(halolower alkyl)-4-piperidinyl]-1H-benzimidazol-2-amine in the presence of an appropriate carbonate, e.g. sodium carbonate and the like.

Compounds of formula (I) which contain at least one hydroxyl-group as a substituent can conveniently be derived from the corresponding phenylmethoxy substituted compounds by subjecting the latter to a catalytic hydrogenation in the presence of an appropriate catalyst, e.g., palladium-on-charcoal and the like. These hydroxyl-derivatives may even so be derived from the corresponding lower alkyloxy substituted analogs by hydrolyzing the latter in acidic medium, using for example hydrogen bromide in acetic acid. The hydroxyl-substituted compounds may in turn be O-alkylated or acylated by reacting the latter with a halide, an alkanoyl halide, an alkyloxycarbonyl halide, an isocyanate and the like. The hydroxyl-substituted compounds may also be converted into halides by reacting therewith a suitable halogenating agent, e.g. thionyl chloride, phosphor pentabromide and the like in the presence of an appropriate solvent, e.g., a trichloromethane and the like.

Amino-substituted compounds may, for example, be derived from the corresponding nitro- and cyano-substituted compounds by reducing the latter, e.g., by catalytic hydrogenation in the presence of an appropriate catalyst, such as, for example, Raney-nickel and the like. The amino-substituted compounds may in turn be N-alkylated or acylated by the reaction thereof with an appropriate alkylating agent or acylating agent, e.g., a halide, an alkanoyl halide, an alkoxycarbonyl halide, an isocyanate and the like.

Secondary and tertiary amino-substituted compounds of formula (I) may be prepared by substituting, for example, an appropriate halo-substituted compound with the desired primary or secondary amine.

Aminocarbonyl-substituted compounds may conveniently be derived from the corresponding esters by reacting the latter with ammonia or an appropriate primary-or a secondary amine in a suitable solvent.

Compounds of formula (I) which contain in their structure a sulfonyl group may easily be derived from the corresponding thio compounds by oxidizing the latter with an appropriate oxydizing agent, e.g. hydrogen peroxide and the like.

In all of the foregoing and in the following preparations, the reaction products may be isolated from the reaction mixture and, if necessary, further purified according to methodologies generally known in the art.

The compounds of formula (I) may be converted to the therapeutically active non-toxic acid addition salt form by treatment with an appropriate acid, such as, for example, an inorganic acid, such as hydrohalic acid, e.g., hydrochloric, hydrobromic and the like, and sulfuric acid, nitric acid, phosphoric acid and the like; or an organic acid, such as, for example, acetic, propanoic, 2-hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The starting materials of formula (II) herein can generally be prepared starting from a thiourea derivative of the formula (X)·wherein R, $R^1$, $R^2$, $R^3$ and n are as previously defined and P is an appropriate protecting group such as, for example, lower alkyloxycarbonyl or phenylmethoxycarbonyl, by subjecting (X) to a cyclodesulfurization reaction to obtain an intermediate of the formula (XI) and thereafter eliminating the protecting group in the usual manner.

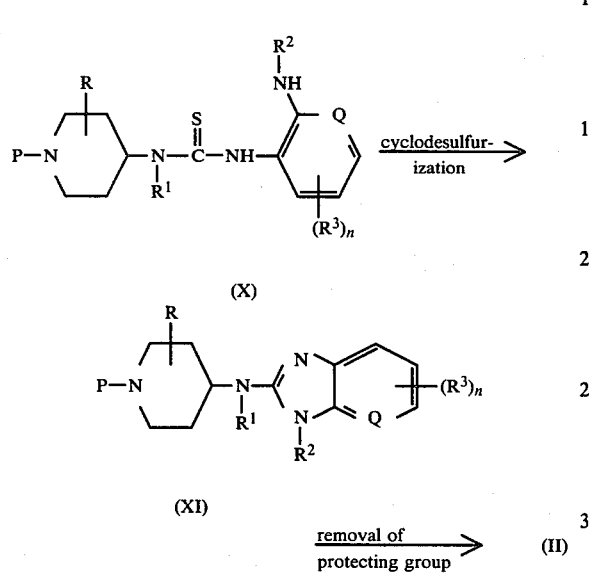

The cyclodesulfurization of (X) to obtain (XI) can be carried out in the same manner as previously described herein for the preparation of the compounds (I) starting from (V). In order to remove the protecting group P there may be used art-known procedures. For example, when said group is a lower alkyloxycarbonyl group it may be removed by alkaline or preferably acid hydrolysis, using for example, hydrobromic acid in glacial acetic acid, and when said protecting group is a phenylmethoxycarbonyl group it may be removed by alkaline or acid hydrolysis or by catalytic hydrogenation using an appropriate catalyst such as palladium-on-charcoal. Intermediates of formula (XI) wherein $R^2$ is other than hydrogen can also be derived from the corresponding (XI) wherein $R^2$ is hydrogen by introducing the desired $R^2$-substituent according to art-known methodologies as described hereinabove in connection with the preparation of compounds (I-a) starting from (I-b).

The thiourea derivatives of formula (X) wherein $R^1$ represents hydrogen, (X-a), can be prepared by the reaction of an appropriate 4-isothiocyanatopiperidine of formula (XII) with an appropriate benzenediamine or pyridinediamine of formula (XIII), e.g., by simply stirring the reactants together in an appropriate organic solvent such as, for example, a lower alkanol, e.g. methanol, ethanol, 2-propanol and the like.

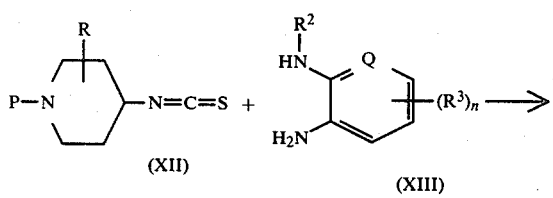

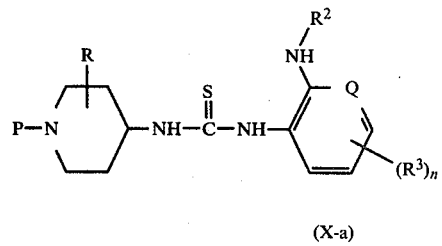

Thiourea derivatives of formula (X) wherein $R^1$ is as previously defined and $R^2$ is hydrogen, (X-b),), can be prepared by the reaction of an appropriate-4-piperidinamine of the formula (XIV) with an appropriate 1-isothiocyanato-2-nitrobenzene of the formula (XV), followed by the reduction of the nitro group of the thus obtained compound (XVI) following well-known nitro-to-amine reduction procedures such as for example by the reaction of (XVI) with nascent hydrogen or by catalytic hydrogenation using an appropriate catalyst such as, for example, palladium-on-charcoal, platinum-on-charcoal and the like, or in the presence of more than one of such catalysts.

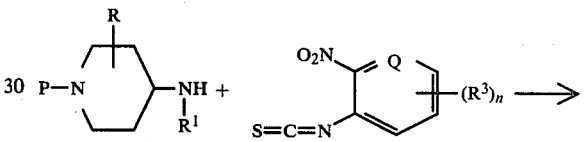

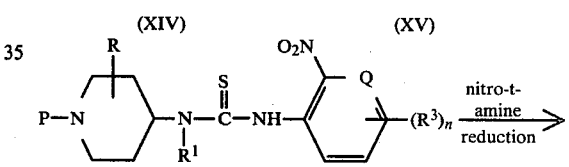

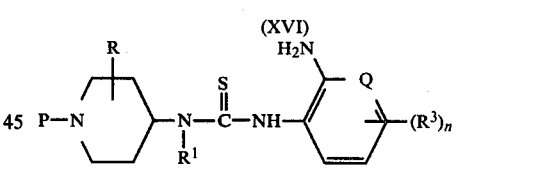

The precursor materials of formula (XIV) herein may be prepared following methods known in the art, e.g., by the reductive amination of the corresponding 4-piperidinone. The 4-isothiocyanatopiperidines of formula (XII) may in turn be prepared starting from the corresponding (XIV) wherein $R^1$ is hydrogen according to standard methods of preparing isothiocyanates starting from primary amines, e.g., by the reaction of the amine with carbon disulfide in alkaline medium and subsequent addition to the reaction mixture of an appropriate lower alkylcarbonochloridate.

The starting materials of formula (XII) wherein P represents a lower alkyloxycarbonyl or phenylmethoxycarbonyl group can also be prepared by the reaction of a corresponding starting material (XII) wherein said P represents phenylmethyl by reacting the latter with an appropriate carbonochloridate.

The starting materials of formula (V) can be prepared using similar procedures as described hereinabove for the preparation of the thiourea derivatives of formula (X) starting however from an appropriate 4-piperidinone or 4-piperidinamine wherein the L-substituent is already present on the piperidine nitrogen atom.

The ultimate starting materials in each of the foregoing preparations are known compounds or they may be prepared by the application of methodologies known in the art for preparing similar known compounds. The preparation of 4-(haloalkyl)-2H-1,4-benzoxazin-3(4H)-ones, for example, by the N-substitution-reaction of 2H-1,4-benzoxazin-3(4H)-one with a dihalolower alkyl group, is described in Belg. Pat. No. 859,415. 1,3-dihydro-1-(3-oxobutyl)-2H-benzimidazol-2-one (XIX) can be prepared by subjecting 1,3-dihydro-1-(1-methylethenyl)-2H-benzimidazol-2-one (XVII) and 3-buten-2-one to a Michael-addition procedure in the presence of a base such as, N,N-diethylethanamine and the like, and subsequently hydrolying the 1,3-dihydro-1-(1-methylethenyl)-3-(3-oxobutyl)-2H-benzimidazol-2-one (XVIII).

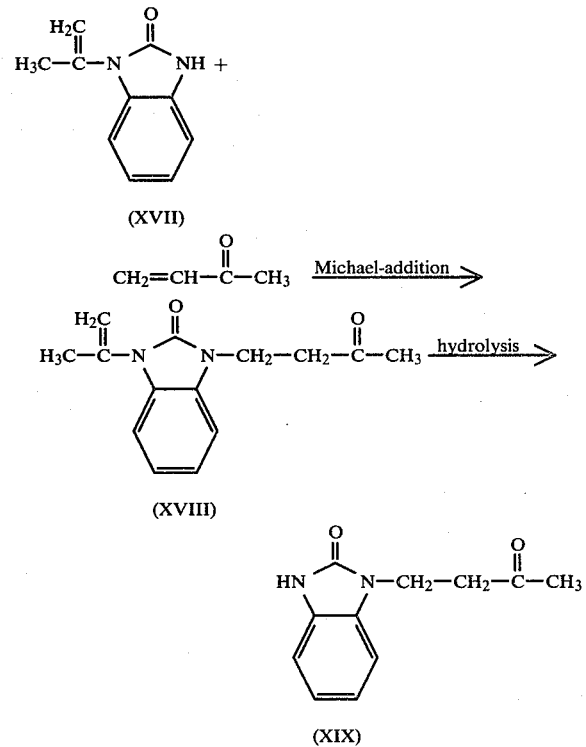

The intermediates of the formulae (II) and (XI) are deemed to be novel and in view of their utility as starting materials in the preparation of the pharmaceutically active compounds of formula (I) they constitute an additional feature of this invention.

The compounds of formula (I) and their pharmaceutically acceptable acid addition salts are potent antihistaminic agents and as such they can be used to prepare valuable medicaments for human and animal therapy. The useful antihistaminic proterties of the compounds of formula (I) were demonstrated in the following test-procedure.

PROTECTION OF RATS FROM COMPOUND 48/80-INDUCED LETHALITY.

Compound 48/80, a mixture of oligomers obtained by condensation of p-methoxy-N-methyl-phenethylamine and formaldehyde has been described as a potent histamine releasing agent (Int. Arch. Allergy, 13, 336 (1958)). The protection from compound 48/80-induced lethal circulatory collapse appears to be a simple way of evaluating quantitatively the antihistaminic activity of test-compounds. Male rats of an inbred Wistar strain, weighing 240–260 g were used in the experiment. After overnight starvation the rats were transferred to conditioned laboratories (temp.=21±1° C., relative humidity=65±5%). The rats were treated subcutaneously or orally with a test compound or with the solvent (NaCl solution, 0.9%). One hour after treatment there was injected intravenously compound 48/80, freshly dissolved in water, at a dose of 0.5 mg/kg (0.2 ml/100 g of body weight). In control experiments, wherein 250 solvent-treated animals were injected with the standard dose of compound 48/80 not more than 2.8% of the animals survived after 4 hours. Survival after 4 hours is therefore considered to be a safe criterion of a protective effect of drug administration. The compounds of formula (I) and the pharmaceutically acceptable acid addition salts thereof were found very active in the above test, protecting the animals against compound 48/80-induced lethality at oral and subcutaneous doses not higher than 2.5 mg/kg. A number of the subject compounds were found effective even at doses as low as 0.16 mg/kg.

In view of their useful antihistaminic activity, the subject compounds may be formulated into various pharmaceutical forms for administration purposes. To prepare the pharmaceutical compositions of this invention, an effective antihistaminic amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example may be prepared in which the carrier comprises saline solution, glucose solution or a mixture of saline and glucose solution. Injectable suspensions may also be prepared in which case appropriate liquid carriers, suspending agents and the like may be employed. Acid addition salt of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following examples are intended to illustrate and not to limit the scope of the present invention. Unless otherwise stated all parts therein are by weight.

A. PREPARATION OF INTERMEDIATES:

EXAMPLE I

A mixture of 102 parts of ethyl 4-oxo-1-piperidinecarboxylate, 50 parts of methanamine and 400 parts of methanol is hydrogenated at normal pressure and at room temperature with 5 parts of palladium-on-charcoal catalyst 10%. After the calculated amount of hydrogen is taken up, the catalyst is filtered off over Hyflo and the filtrate is evaporated, yielding 111 parts of ethyl 4-(methylamino)-1-piperidinecarboxylate as a residue.

To a stirred and cooled mixture of 4 parts of sodium hydroxide in 60 parts of water are added successively 7.9 parts of carbon disulfide and 17.2 parts of ethyl 4-amino-1-piperidinecarboxylate at a temperature below 10° C. Stirring is continued for 30 minutes at this temperature. Then there are added dropwise 10.9 parts of ethyl carbonochloridate (exothermic reaction: temp. rises to about 35° C.). Upon completion, stirring is continued for 2 hours at 60° C. The reaction mixture is cooled and the product is extracted with methylbenzene. The extract is dried, filtered and evaporated, yielding 22 parts (100%) of ethyl 4-isothiocyanato-1-piperidinecarboxylate as a residue.

By repeating the procedure of the second step there are also prepared starting from an appropriate amine:
4-isothiocyanato-1-(phenylmethyl)piperidine; and
1-[4,4-bis(4-fluorophenyl)butyl]-4-isothiocyanatopiperidine; mp. 92° C.

EXAMPLE II

To a stirred solution of 28.4 parts of 4-isothiocyanato-1-(phenylmethyl)piperidine in 315 parts of methylbenzene are added dropwise 41 parts of (phenylmethyl) carbonochloridate at room temperature. Upon completion, the whole is heated to reflux and stirring is continued overnight at reflux temperature. The reaction mixture is cooled and the solvent is evaporated. The residue is purified by column-chromatography over silica gel using trichloromethane as eluent. The pure fractions are collected and the eluent is evaporated, yielding 32 parts (97%) of (phenylmethyl) 4-isothiocyanato-1-piperidinecarboxylate as a residue.

EXAMPLE III

A mixture of 9.7 parts of 4-fluorobenzenemethanamine hydrochloride, 9.4 parts of 2-chloro-3-nitropyridine, 10.6 parts of sodium carbonate, 0.1 parts of potassium iodide and 90 parts of N,N-dimethylformamide is stirred for 1 hour at 90° C. The reaction mixture is cooled and poured onto water. The precipitated product is filtered off and crystallized from 2-propanol, yielding 10.5 parts (71%) of N-(4-fluorophenylmethyl)-3-nitro-2-pyridinamine; mp. 76° C.

A mixture of 10.5 parts of N-(4-fluorophenylmethyl)-3-nitro-2-pyridinamine and 200 parts of methanol is hydrogenated at normal pressure and at room temperature with 2 parts of Raney-nickel catalyst. After the calculated amount of hydrogen is taken up, the catalyst is filtered off and the filtrate is evaporated, yielding 9.3 parts (100%) of $N^2$-(4-fluorophenylmethyl)-2,3-pyridinediamine as a residue.

Following the same procedure and using equivalent amounts of the appropriate starting materials there are also prepared:
$N^1$-(phenylmethyl)-4-(trifluoromethyl)-1,2-benzenediamine; and
4-chloro-$N^1$-(4-fluorophenylmethyl)-1,2-benzenediamine.

EXAMPLE IV

A mixture of 34.8 parts of 1,3-dihydro-1-(1-methylethenyl)-2H-benzimidazol-2-one, 28 parts of 3-buten-2-one, 20.2 parts of N,N-diethylethanamine and 270 parts of tetrahydrofuran is stirred and refluxed over week-end. The reaction mixture is evaporated, yielding 48.8 parts (100%) of 1,3-dihydro-1-(1-methylethenyl)-3-(3-oxobutyl)-2H-benzimidazol-2-one as a residue.

A mixture of 48.8 parts of 1,3-dihydro-1-(1-methylethenyl)-3-(3-oxobutyl)-2H-benzimidazol-2-one, 12 parts of 2-propanol, saturated with gaseous hydrogen chloride and 240 parts of 2-propanol is stirred for 3 hours at room temperature. The precipitated product is filtered off, washed with 2,2'-oxybispropane and dried, yielding 30 parts (73.4%) of 1,3-dihydro-1-(3-oxobutyl)-2H-benzimidazol-2-one.

EXAMPLE V

To a stirred mixture of 9 parts of 2H-1,4-benzoxazin-3(4H)-one, 0.9 parts of N,N,N-triethylbenzenemethanaminium chloride, 9 parts of sodium hydroxide solution 50% and 24 parts of water are added 10.4 parts of 1-bromo-3-chloropropane at 30° C. The whole is heated to 90° C. and stirring is continued for 3 hours at this temperature. The reaction mixture is cooled to about 70° C., methylbenzene is added and the whole is stirred overnight at room temperature. The organic phase is separated, dried, filtered and evaporated, yielding 10 parts of 4-(3-chloropropyl)-2H-1,4-benzoxazin-3(4H)-one as a residue.

EXAMPLE VI

A mixture of 10.6 parts of ethyl 4-isothiocyanato-1-piperidinecarboxylate, 11.6 parts of 4-chloro-$N^1$-(phenylmethyl)-1,2-benzenediamine and 90 parts of tetrahydrofuran is stirred overnight at room temperature. The reaction mixture is evaporated, yielding 21 parts (100%) of ethyl 4-[{[{5-chloro-2-[(phenylmethyl)amino]phenyl}amino]thioxomethyl}amino]-1-piperidinecarboxylate; mp. 162° C.

EXAMPLE VII

Following the procedure of Example VI and using equivalent amounts of the appropriate starting materials there are prepared:
ethyl 4-{[(2-amino-5-chlorophenyl)aminothioxomethyl]amino}-1-piperidinecarboxylate; mp. 162.2° C.;
ethyl 4-{[(2-aminophenyl)aminothioxomethyl]amino}-1-piperidinecarboxylate as a residue;

ethyl 4-{[(2-amino-5-methylphenyl)aminothioxomethyl]amino}-1-piperidinecarboxylate as a residue;
ethyl 4-[{[{2-[(phenylmethyl)amino]-3-pyridinyl}-amino]thioxomethyl}amino]-1-piperidinecarboxylate; mp. 146.7° C.;
ethyl 4-{[{2-[(phenylmethyl)amino]-5-(trifluoromethyl)phenyl}amino]thioxomethylamino}-1-piperidinecarboxylate as a residue;
ethyl 4-[{[(2-amino-4-fluorophenyl)amino]thioxomethyl}amino]-1-piperidinecarboxylate as a residue;
ethyl 4-[{[{5-chloro-2-[(4-fluorophenylmethyl)amino]-phenyl}amino]thioxomethyl}amino]-1-piperidineearboxylate as a residue;
(phenylmethyl) 4-[{2-[(4-fluorophenylmethyl)amino]-3-pyridinylamino}thioxomethylamino]-1-piperidinecarboxylate;
N-(2-nitrophenyl)-N'-[1-(2-phenylethyl)-4-piperidinyl]-N'-(phenylmethyl)thiourea; mp. 151.1° C.;
N-{1-[4,4-bis(4-fluorophenyl)butyl]-4-piperidinyl}-N'-phenylthiourea; mp. 90° C.;
ethyl 4-[{[(2-amino-3-pyridinyl)amino]thioxomethyl}-amino]-1-piperidinecarboxylate; mp. 176.9° C.;
4-[{[(2-phenylamino)phenyl]aminothioxomethyl}-amino]-1-piperidinecarboxylate; mp. 154.2° C.; and
ethyl 4-{[{[2-(4-fluorophenylamino)phenyl]amino}thioxomethyl]-amino}-1-piperidinecarboxylate as a residue.

EXAMPLE VIII

A mixture of 21.6 parts of 1-isothiocyanato-2-nitrobenzene and 45 parts of tetrahydrofuran is stirred till all solid enters solution. Then there are added 29.5 parts of N-(1-methylethyl)-1-(2-phenylethyl)-4-piperidinamine and 160 parts of ethanol and the whole is stirred overnight at room temperature. The reaction mixture is evaporated and the residue is crystallized from 2-propanol. The product is filtered off and dried, yielding 43 parts (84%) of N-(1-methylethyl)-N'-(2-nitrophenyl)-N-[1-(2-phenylethyl)-4-piperidinyl]thiourea; mp. 100.6° C.

EXAMPLE IX

Following the procedure of Example VIII the following thiourea derivatives are prepared by the reaction of an appropriate 4-piperidinamine with an appropriate 1-isothiocyanato-2-nitrobenzene.
ethyl 4-[methyl-{[(2-nitrophenyl)amino]thioxomethyl}-amino]-1-piperidinecarboxylate;
ethyl 4-{butyl[(2-nitrophenyl)aminothioxomethyl]amino}-1-piperidinecarboxylate as a residue;
N-ethyl-N'-(2-nitrophenyl)-N-[1-(2-phenylethyl)-4-piperidinyl]-thiourea;
N-(2-nitrophenyl)-N'-[1-(2-phenylethyl)-4-piperidinyl]-N'-propylthiourea; mp. 90.3° C.;
N-cyclopropyl-N'-(2-nitrophenyl)-N-[1-(2-phenylethyl)-4-piperidinyl]thiourea; mp. 150.1° C.; and
cis+trans-methyl 3-methyl-4-[{[(2-nitrophenyl)amino]-thioxomethyl}amino]-1-piperidinecarboxylate; mp. 157.5° C.

EXAMPLE X

A mixture of 43 parts of N-(1-methylethyl)-N'-(2-nitrophenyl)-N-[1-(2-phenylethyl)-4-piperidinyl]thiourea and 800 parts of methanol, saturated with ammonia is hydrogenated at normal pressure and at room temperature with 6 parts of palladium-on-charcoal catalyst 10% and 6 parts of platinum-on-charcoal catalyst 5%. After the calculated amount of hydrogen is taken up, the catalysts are filtered off over Hyflo and the filtrate is evaporated, yielding 39 parts (100%) of N-(2-aminophenyl)-N'-(1-methylethyl)-N'-[1-(2-phenylethyl)-4-piperidinyl]thiourea as a residue.

EXAMPLE XI

Following the procedure of Example X and using an equivalent amount of an appropriate nitro-compound as a starting material, there are prepared:
ethyl 4-[{[(2-aminophenyl)amino]thioxomethyl}methylamino]-1-piperidinecarboxylate;
ethyl 4-{[(2-aminophenyl)aminothioxomethyl]-butylamino}-1-piperidinecarboxylate;
N-(2-aminophenyl)-N'-[1-(2-phenylethyl)-4-piperidinyl]thiourea;
N-(2-aminophenyl)-N'-[1-(2-phenylethyl)-4-piperidinyl]-N'-propylthiourea;
N-(2-aminophenyl)-N'-cyclopropyl-N'-[1-(2-phenylethyl)-4-piperidinyl]thiourea;
methyl 4-{[(2-aminophenyl)amino]thioxomethylamino}-3-methyl-1-piperidinecarboxylate;
N-(2-aminophenyl)-N'-[1-(2-phenylethyl)-4-piperidinyl]-N'-(phenylmethyl)thiourea as a residue.

EXAMPLE XII

A mixture of 23 parts of (phenylmethyl) 4-[{2-[(4-fluorophenylmethyl)amino]-3-pyridinylamino}thioxomethylamino]-1-piperidinecarboxylate, 17 parts of mercury oxide, 0.1 parts of sulfur and 450 parts of tetrahydrofuran is stirred and refluxed for 1 hour. The reaction mixture is filtered over Hyflo and the filtrate is evaporated. The residue is crystallized from a mixture of 4-methyl-2-pentanone and 2,2'-oxybispropane. The product is filtered off and dried, yielding 20 parts (93%) of (phenylmethyl) 4-[3-(4-fluorophenylmethyl)-3H-imidazo[4,5-b]pyridin-2-ylamino]-1-piperidinecarboxylate; mp. 130° C.

EXAMPLE XIII

Following the procedure of Example XII and using equivalent amounts of the appropriate starting materials there are prepared:
ethyl 4-[(1H-benzimidazol-2-yl)methylamino]-1-piperidinecarboxylate;
ethyl 4-[(1H-benzimidazol-2-yl)butylamino]-1-piperidinecarboxylate; mp. 225.9° C.
ethyl 4-[1-(phenylmethyl)-5-(trifluoromethyl)-1H-benzimidazol-2-ylamino]-1-piperidinecarboxylate; mp. 200° C.;
ethyl 4-(5-fluoro-1H-benzimidazol-2-ylamino)-1-piperidinecarboxylate; mp. 227.5° C.;
ethyl 4-[5-chloro-1-(phenylmethyl)-1H-benzimidazol-2-ylamino]-1-piperidinecarboxylate; mp. 211.9° C.;
ethyl 4-[3-(phenylmethyl)-3H-imidazo[4,5-b]pyridin-2-ylamino]-1-piperidinecarboxylate; mp. 148.6° C.;
ethyl 4-[5-chloro-1-(4-fluorophenylmethyl)-1H-benzimidazol-2-ylamino]-1-piperidinecarboxylate; mp. 215.8° C.;
methyl 4-(1H-benzimidazol-2-ylamino)-3-methyl-1-piperidinecarboxylate; mp. 155° C.;
ethyl 4-[3-(4-fluorophenylmethyl)-3H-imidazo[4,5-b]pyridin-2-ylamino]-1-piperidinecarboxylate; mp. 134.4° C.;
ethyl 4-[(3-imidazo[4,5-b]pyridin-2-yl)amino]-1-piperidinecarboxylate; mp. 216.1° C.;
ethyl 4-(1-phenyl-1H-benzimidazol-2-ylamino)-1-piperidinecarboxylate; mp. 137° C.; and ethyl 4-[1-(4-fluorophenyl)-1H-benzimidazol-2-ylamino]-1-piperidinecarboxylate; mp. 153° C.

EXAMPLE XIV

A mixture of 28 parts of ethyl 4-{[(2-aminophenyl)aminothioxomethyl]amino}-1-piperidinecarboxylate, 112 parts of iodomethane and 240 parts of ethanol is stirred and refluxed for 8 hours. The reaction mixture is evaporated and the residue is taken up in water. The whole is alkalized with ammonium hydroxide and the product is extracted with dichloromethane. The extract is dried, filtered and evaporated. The residue is crystallized from a mixture of 2-propanol and 2,2'-oxybispropane. The product is filtered off and dried, yielding 7 parts (28%) of ethyl 4-(1H-benzimidazol-2-ylamino)-1-piperidinecarboxylate.

Following the same procedure and using equivalent amounts of the appropriate starting materials there are prepared:
ethyl 4-(5-chloro-1H-benzimidazol-2-ylamino)-1-piperidinecarboxylate; mp. 234.1° C.; and
ethyl 4-(5-methyl-1H-benzimidazol-2-ylamino)-1-piperidinecarboxylate.

EXAMPLE XV

A mixture of 19 parts of methyl 4-(1H-benzimidazol-2-ylamino)-3-methyl-1-piperidinecarboxylate, 11 parts of 1-(chloromethyl)-4-fluorobenzene, 6 parts of sodium carbonate and 135 parts of N,N-dimethylformamide is stirred and heated overnight at 70° C. The reaction mixture is cooled and poured onto water. The product is extracted three times with methylbenzene. The combined extracts are dried, filtered and evaporated. The residue is purified by column-chromatography over silica gel using a mixture of trichloromethane and methanol (96:4 by volume) as eluent. The pure fractions are collected and the eluent is evaporated. The residue is crystallized from a mixture of 2-propanone and 2,2'-oxybispropane. The product is filtered off and dried, yielding 8 parts (38%) of methyl 4-[1-(4-fluorophenylmethyl)-1H-benzimidazol-2-ylamino]-3-methyl-1-piperidinecarboxylate; mp. 172.5° C.

EXAMPLE XVI

Following the procedure of Example (XIII) the following 4-(1-$R^2$-1H-benzimidazol-2-ylamino)-1-piperidinecarboxylates are prepared by alkylating the corresponding 4-(1H-benzimidazol-2-ylamino)-1-piperidinecarboxylate with an appropriate chloride, bromide or iodide of the formula $R^2X$:

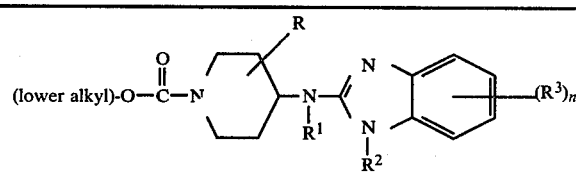

| lower alkyl | R | $R^1$ | $R^2$ | $(R^3)_n$ | melting point |
|---|---|---|---|---|---|
| $C_2H_5$ | H | H | $CH_3$ | H | 166.7° C. |
| $C_2H_5$ | H | H | $CH_3$ | 5(6)-$CH_3$ | 142.0° C. |
| $C_2H_5$ | H | H | $C_2H_5$ | H | — |
| $C_2H_5$ | H | H | n. $C_3H_7$ | H | — |
| $C_2H_5$ | H | H | i. $C_3H_7$ | H | — |
| $C_2H_5$ | H | H | n. $C_4H_9$ | H | — |
| $C_2H_5$ | H | H | n. $C_5H_{11}$ | H | — |
| $C_2H_5$ | H | H | n. $C_6H_{13}$ | H | — |
| $C_2H_5$ | H | H | n. $C_7H_{15}$ | H | — |
| $C_2H_5$ | H | H | ⌧ (cyclopropylmethyl) | H | — |
| $C_2H_5$ | H | H | 4-Br—$C_6H_4$—$CH_2$ | H | — |
| $C_2H_5$ | H | H | $C_6H_5$—$CH_2$ | 5(6)-$CH_3$ | 179.3° C. |
| $C_2H_5$ | H | H | $C_6H_5$—$CH_2$ | H | — |
| $C_2H_5$ | H | H | 4-$CH_3$—$C_6H_4$—$CH_2$ | H | 177.7° C. |
| $C_2H_5$ | H | H | 4-F—$C_6H_4$—$CH_2$ | H | — |
| $C_2H_5$ | H | H | 2-F—$C_6H_4$—$CH_2$ | H | 176.0° C. |
| $C_2H_5$ | H | H | 4-F—$C_6H_4$—$CH_2$ | 5(6)-F | 182.5° C. |
| $C_2H_5$ | H | H | $C_6H_5$—$CH_2$ | 5(6)-F | 184.0° C. |
| $CH_3$ | $CH_3$ | H | $C_6H_5$—$CH_2$ | H | 191.0° C. (cis+trans-isomer) |
| $C_2H_5$ | H | H | 4-$NO_2$—$C_6H_4$—$CH_2$ | H | — |
| $C_2H_5$ | H | $CH_3$ | $C_6H_5$—$CH_2$ | H | 258.0° C.(HCl-salt) |
| $C_2H_5$ | H | H | 4-F-2—$CH_3$—$C_6H_3$—$CH_2$ | H | — |

EXAMPLE XVII

A mixture of 7 parts of ethyl 4-{[5(6)-fluoro-1-(4-fluorophenylmethyl)-1H-benzimidazol-2-yl]amino}-1-piperidinecarboxylate and 300 parts of hydrobromic acid solution 48% in glacial acetic acid is stirred and refluxed for 1 hour. The reaction mixture is evaporated and the residue is boiled in 2-propanol. 2,2'-Oxybispropane is added and upon cooling, the product is allowed to crystallize. It is filtered off and dried, yielding 7.2 parts (88.2%) of 5(6)-fluoro-1-(4-fluorophenylmethyl)-N-(4-piperidinyl)-1H-benzimidazol-2-amine dihydro bromide; mp. 285.6° C.

EXAMPLE XVIII

Following the procedure of Example the following 1-$R^2$-N-(4-piperidinyl)-1H-benzimidazol-2-amines are prepared by hydrolysing the corresponding methyl or ethyl 1-piperidinecarboxylates.

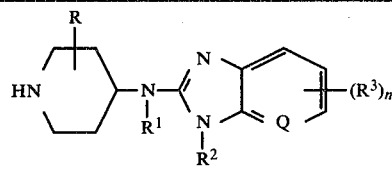

| R | $R^1$ | $R^2$ | $(R^3)_n$ | Q | Base or Salt form | melting point |
|---|---|---|---|---|---|---|
| H | H | H | 5-Cl | CH | 2HBr | — |
| H | H | H | H | CH | 2HBr | — |
| H | H | $CH_3$ | 5(6)-$CH_3$ | CH | 2HBr | — |
| H | H | H | 5-$CH_3$ | CH | 2HBr | — |
| H | H | $CH_3$ | H | CH | 2HBr | — |
| H | H | $C_2H_5$ | H | CH | 2HBr . ½$H_2O$ | 334°–338° C. |
| H | H | $nC_3H_7$ | H | CH | 2HBr | — |
| H | H | $C_6H_5$—$CH_2$ | H | CH | 2HBr | — |
| H | H | $nC_5H_{11}$ | H | CH | base | — |
| H | H | $nC_7H_{15}$ | H | CH | base | — |
| H | H | $nC_4H_9$ | H | CH | base | — |
| H | H | $nC_6H_{13}$ | H | CH | base | — |
| H | H | cyclopentyl | H | CH | base | — |
| H | H | $iC_3H_7$ | H | CH | base | — |
| H | $CH_3$ | H | H | CH | 2HBr . $H_2O$ | — |
| H | H | 2-Cl—$C_6H_4$—$CH_2$ | H | CH | base | — |
| H | H | 4-Cl—$C_6H_4$—$CH_2$ | H | CH | 2HBr . $H_2O$ | — |
| H | H | 4-Br—$C_6H_4$—$CH_2$ | H | CH | 2HBr . $H_2O$ | >300° C. |
| H | H | 4-$CH_3$—$C_6H_4$—$CH_2$ | H | CH | 2HBr | — |
| H | H | 4-F—$C_6H_4$—$CH_2$ | H | CH | 2HBr | — |
| H | $nC_4H_9$ | H | H | CH | 2HBr . $H_2O$ | 223.1° C. |
| H | H | 2-F—$C_6H_4$—$CH_2$ | H | CH | 2HBr | — |
| H | H | $C_6H_5$—$CH_2$ | 5-$CF_3$ | CH | 2HBr | — |
| H | H | $C_6H_5$—$CH_2$ | 5-Cl | CH | 2HBr | >260° C. |
| H | H | $C_6H_5$—$CH_2$ | H | N | 2HCl . $H_2O$ | 298.1° C. |
| H | H | 4-F—$C_6H_4$—$CH_2$ | 5-Cl | CH | 2HBr | >260° C. |
| H | H | 4-F—$C_6H_4$—$CH_2$ | 5(6)-$CH_3$ | CH | 2HBr | — |
| H | H | $C_6H_5$—$CH_2$ | 5(6)-$CH_3$ | CH | 2HBr | — |
| H | H | $C_6H_5$—$CH_2$ | 5(6)-F | CH | 2HBr | >260° C. |
| 3-$CH_3$ | H | 4-F—$C_6H_4$—$CH_2$ | H | CH | 2HBr | — |
| 3-$CH_3$ | H | $C_6H_5$—$CH_2$ | H | CH | 2HBr . $H_2O$ | 250.2° C. (cis + trans-isomer) |
| H | H | $C_6H_5$ | H | CH | 2HBr . $H_2O$ | >300° C. |
| H | H | 4-F—$C_6H_4$ | H | CH | 2HBr | >300° C. |
| H | H | 4-$NO_2$—$C_6H_4$—$CH_2$ | H | CH | 2HBr | — |
| H | H | 4-F-2-$CH_3$—$C_6H_3$—$CH_2$ | H | CH | 2HBr | — |

EXAMPLE XIX

A mixture of 20 parts of (phenylmethyl) 4-[3-(4-fluorophenylmethyl)-3H-imidazo[4,5-b]pyridine-2-ylamino]-1-piperidinecarboxylate and 160 parts of methanol is hydrogenated at normal pressure and at room temperature with 2 parts of palladium-on-charcoal catalyst 10%. After the calculated amount of hydrogen is taken up, the catalyst is filtered off and the filtrate is evaporated. The residue is boiled in 2,2'-oxybispropane. The undissolved product is filtered off and converted into the hydrochloride salt in 2-propanol. The salt is filtered off and dried, yielding 12 parts of 3-(4-fluorophenylmethyl)-N-(4-piperidinyl)-3H-imidazo[4,5-b]pyridin-2-amine dihydrochloride monohydrate; mp. 269.7° C.

B. PREPARATION OF FINAL PRODUCTS:

EXAMPLE XX

A mixture of 2 parts of 2-(bromoethoxy)benzene, 3 parts of 1-(phenylmethyl)-N-(4-piperidinyl)-1H-benzimidazol-2-amine, 2 parts of sodium carbonate, 0.1 parts of potassium iodide and 90 parts of N,N-dimethylformamide is stirred overnight at 70° C. The reaction mixture is cooled and poured onto water. The product is extracted with methylbenzene. The extract is dried, filtered and evaporated. The residue is converted into the hydrochloride salt in 2-propanone. The salt is filtered off and dried, yielding 3.5 parts (70%) of N-[1-(2-phenoxyethyl)-4-piperidinyl]-1-(phenylmethyl)-1H-benzimidazol-2-amine dihydrochloride monohydrate; mp. 197.6° C.

EXAMPLE XXI

Following the procedure of Example XX and using equivalent amounts of the appropriate starting materials the following compounds are prepared in free base form or in the form of an acid addition salt after reacting the free base with an appropriate acid.

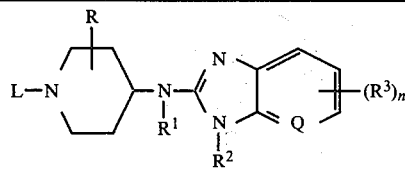

| L | R | R¹ | R² | $(R^3)_n$ | Q | Base or Salt form | melting point |
|---|---|---|---|---|---|---|---|
| $C_6H_5-(CH_2)_2$ | H | H | $CH_3$ | H | CH | $2HCl \cdot \frac{1}{2} H_2O$ | 298.3° C. |
| $C_6H_5-(CH_2)_2$ | H | H | $C_2H_5$ | H | CH | base | 192.8° C. |
| $C_6H_5-(CH_2)_2$ | H | H | $nC_3H_7$ | H | CH | $2HCl \cdot \frac{1}{2} H_2O$ | 278.8° C. |
| $C_6H_5-(CH_2)_2$ | H | H | $C_6H_5-CH_2$ | H | CH | base | 141.9° C. |
| $C_6H_5-(CH_2)_2$ | H | H | $nC_5H_{11}$ | H | CH | $2HCl \cdot H_2O$ | 243.5° C. |
| $C_6H_5-(CH_2)_2$ | H | H | $nC_7H_{15}$ | H | CH | $2HCl \cdot H_2O$ | 212.8° C. |
| $C_6H_5-(CH_2)_2$ | H | H | $nC_4H_9$ | H | CH | $2HCl \cdot \frac{1}{2} H_2O$ | 274.4° C. |
| $C_6H_5-(CH_2)_2$ | H | H | $nC_6H_{13}$ | H | CH | $2HCl \cdot H_2O$ | 224.2° C. |
| $C_6H_5-(CH_2)_2$ | H | H | cyclopentyl-CH₂ | H | CH | $2HCl \cdot \frac{1}{2} H_2O$ | 285.6° C. |
| $C_6H_5-(CH_2)_2$ | H | H | $iC_3H_7$ | H | CH | $2HCl$ | 295.8° C. |
| $C_6H_5-(CH_2)_2$ | H | $CH_3$ | H | H | CH | $2HCl$ | 299.6° C. |
| $C_6H_5-(CH_2)_2$ | H | H | $2-Cl-C_6H_4-CH_2$ | H | CH | $2HCl \cdot \frac{1}{2} H_2O$ | 244.4° C. |
| $C_6H_5-(CH_2)_2$ | H | H | $4-Br-C_6H_4-CH_2$ | H | CH | $2HCl \cdot H_2O$ | 251.5° C. |
| $C_6H_5-(CH_2)_2$ | H | H | $4-CH_3-C_6H_4-CH_2$ | H | CH | $2HCl \cdot H_2O$ | 191.4° C. |
| $C_6H_5-(CH_2)_2$ | H | H | $4-F-C_6H_4-CH_2$ | H | CH | $2HCl$ | 281.1° C. |
| $C_6H_5-(CH_2)_2$ | H | $nC_4H_9$ | H | H | CH | base | 183.4° C. |
| $C_6H_5-(CH_2)_2$ | H | H | $2-F-C_6H_4-CH_2$ | H | CH | base | 138.6° C. |
| $C_6H_5-(CH_2)_2$ | H | H | H | H | CH | base | 192.1° C. |
| $C_6H_5-(CH_2)_2$ | H | H | $C_6H_5-CH_2$ | $5-CF_3$ | CH | $2HCl$ | 264.7° C. |
| $C_6H_5-(CH_2)_2$ | H | H | $4-F-C_6H_4-CH_2$ | $5-Cl$ | CH | base | 168.3° C. |
| $C_6H_5-(CH_2)_2$ | H | H | $4-F-C_6H_4-CH_2$ | $5(6)-CH_3$ | CH | base | 203°–215° C. |
| $C_6H_5-(CH_2)_2$ | H | H | $C_6H_5-CH_2$ | $5(6)-CH_3$ | CH | base | 181.9° C. |
| $C_6H_5-(CH_2)_2$ | H | H | $C_6H_5-CH_2$ | $5(6)-F$ | CH | base $\cdot \frac{1}{2} H_2O$ | 146.1° C. |
| $C_6H_5-(CH_2)_2$ | H | H | $4-F-C_6H_4-CH_2$ | H | N | base | 193.2° C. |
| $C_6H_5-(CH_2)_2$ | $CH_3$ | H | $C_6H_5-CH_2$ | H | CH | $2HCl \cdot H_2O$ | 297.9° C. (cis + trans-isomer) |
| $C_6H_5-(CH_2)_2$ | $CH_3$ | H | $4-F-C_6H_4-CH_2$ | H | CH | $2HCl \cdot H_2O$ | 220.3° C. (cis + trans-isomer) |
| $4-NO_2-C_6H_4-(CH_2)_2$ | H | H | $4-F-C_6H_4-CH_2$ | H | CH | base | 162.7° C. |
| $C_6H_5-(CH_2)_3$ | H | H | $C_6H_5-CH_2$ | H | CH | $2HCl \cdot H_2O$ | 197.1° C. |
| $CH_2=CH-CH_2$ | H | H | $C_2H_5$ | H | CH | $2HNO_3 \cdot \frac{1}{2} H_2O$ | 258.1° C. |
| $CH_2=CH-CH_2$ | H | H | $C_6H_5-CH_2$ | H | CH | $2HCl \cdot H_2O$ | 261.9° C. |
| $C_6H_5-O-(CH_2)_3$ | H | H | $C_6H_5-CH_2$ | H | CH | $2HCl \cdot \frac{1}{2} H_2O$ | 208.8° C. |
| $C_6H_5-O-(CH_2)_3$ | H | H | $4-F-C_6H_4-CH_2$ | H | CH | base | 144.5° C. |
| $C_6H_5-O-(CH_2)_3$ | H | H | $4-F-C_6H_4-CH_2$ | H | N | base | 157.6° C. |
| $C_6H_5-O-(CH_2)_3$ | $CH_3$ | H | $4-F-C_6H_4-CH_2$ | H | CH | $2(COOH)_2H_2O$ | 141.3° C. |
| $(C_6H_5)_2CH-(CH_2)_2$ | H | H | $C_6H_5-CH_2$ | H | CH | base | 173.8° C. |
| $nC_4H_9$ | H | H | $C_6H_5-CH_2$ | H | CH | $2HCl \cdot H_2O$ | 273.3° C. |
| $C_6H_5-CO-CH_2$ | H | H | $C_6H_5-CH_2$ | H | CH | $2HNO_3 \cdot 3H_2O$ | 135.6° C. |
| $(C_6H_5)_2CH$ | H | H | $C_6H_5-CH_2$ | H | CH | base | 203.7° C. |
| $C_6H_5-CH(CH_3)$ | H | H | $C_6H_5-CH_2$ | H | CH | base | 154.0° C. |
| $C_6H_5-CH(CH_3)-CH_2$ | H | H | $C_6H_5-CH_2$ | H | CH | $2HNO_3 \cdot H_2O$ | 159.0° C. |
| $C_6H_5-CH(CH_3)$ | H | H | $4-F-C_6H_4-CH_2$ | H | CH | base | 170°–172.8° C. |
| $C_6H_5-CH(CH_3)-CH_2$ | H | H | $4-F-C_6H_4-CH_2$ | H | CH | $2HNO_3-2H_2O$ | 155.4° C. |

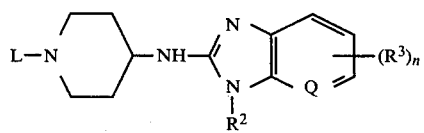

| L | R² | $(R^3)_n$ | Q | Base or salt form | melting point |
|---|---|---|---|---|---|
| $4-CH_3O-C_6H_4-O-(CH_2)_3$ | $4-F-C_6H_4-CH_2$ | H | CH | base | 143.1° C. |
| $C_6H_5-CH=CH-CH_2$ | $4-F-C_6H_4-CH_2$ | H | CH | base $\cdot H_2O$ | 155.5° C. |
| $C_6H_5-CH=CH-CH_2$ | $C_6H_5-CH_2$ | H | CH | $2HCl \cdot H_2O$ | 192.4° C. |
| $C_6H_5-CH=CH-CH_2$ | $C_2H_5$ | H | CH | $2HNO_3 \cdot 2H_2O$ | 136.0° C. |
| $C_6H_5-CH=CH-CH_2$ | $4-F-C_6H_4-CH_2$ | H | N | base | 152.8° C. |
| $C_6H_5-O-(CH_2)_4$ | $4-F-C_6H_4-CH_2$ | H | CH | base | 150.7° C. |
| $4-F-C_6H_4-CO-(CH_2)_3$ | $C_6H_5-CH_2$ | H | CH | $2HCl \cdot \frac{1}{2} H_2O$ | 269.1° C. |

-continued

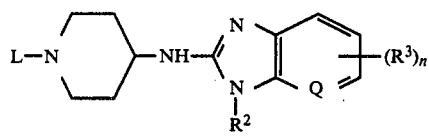

| L | R² | (R³)ₙ | Q | Base or salt form | melting point |
|---|---|---|---|---|---|
| 4-F—C₆H₄—CO—(CH₂)₃ | C₂H₅ | H | CH | 2HCl | 293.1° C. |
| C₆H₅—CH₂ | CH₃ | H | CH | 2HCl . 2H₂O | 241.0° C. |
| C₆H₅—CH₂ | C₆H₅—CH₂ | H | CH | 2HNO₃ . 2H₂O | 147.2° C. |
| 4-F—C₆H₄—CH₂ | C₆H₅—CH₂ | H | CH | base | 152.1° C. |
| C₆H₅(CH₂)₂ | 4-Cl—C₆H₄—CH₂ | H | CH | 2HCl . ½H₂O | 277.1° C. |
| 4-F—C₆H₄—(CH₂)₂ | 4-F—C₆H₄—CH₂ | H | CH | 2HCl . ½H₂O | 283.7° C. |
| 4-F—C₆H₄—(CH₂)₂ | C₆H₅—CH₂ | H | CH | base | 112.5° C. |
| 3-CF₃—C₆H₄—(CH₂)₂ | C₆H₅—CH₂ | H | CH | base | 140.3° C. |
| (4-F—C₆H₄)₂CH—(CH₂)₃— | H | H | CH | 2HCl . ½H₂O | 279.4° C. |
| (4-F—C₆H₄)₂CH—(CH₂)₃— | H | 5-Cl | CH | 2HCl | 194.8° C. |
| (4-F—C₆H₄)₂CH—(CH₂)₃— | H | 5-CH₃ | CH | 2HCl . ½CH₃CHOHCH₃ | 171.8° C. |
| (4-F—C₆H₄)₂CH—(CH₂)₃— | C₆H₅—CH₂ | H | CH | 2HNO₃.H₂O | 230.9° C. |
| (4-F—C₆H₄)₂CH—(CH₂)₃— | CH₃ | H | CH | 2HCl . H₂O | 271.7° C. |
| (4-F—C₆H₄)₂CH—(CH₂)₃— | CH₃ | 5(6)-CH₃ | CH | 2HCl . H₂O | 245.8° C. |
| (4-F—C₆H₄)₂CH—(CH₂)₃ | C₂H₅ | H | CH | 2HCl . 2H₂O | 208.6° C. |
| ![benzimidazolone-(CH₂)₂] | C₆H₅—CH₂ | H | CH | base | 237.5° C. |
| ![benzimidazolone-(CH₂)₂] | C₂H₅ | H | CH | base | 227.0° C. |
| ![CH₃-N tetrazinone N-(CH₂)₂] | 4-F—C₆H₄—CH₂ | H | CH | 2HCl . H₂O | 192.9° C. |
| ![C₂H₅-N tetrazinone N-(CH₂)₂] | C₆H₅—CH₂ | H | CH | 2HCl . H₂O | 170.9° C. |
| ![C₂H₅-N tetrazinone N-(CH₂)₂] | 4-F—C₆H₄—CH₂ | H | CH | base | 146.5° C. |
| ![C₆H₅-N tetrazinone N-(CH₂)₂] | CH₃ | H | CH | 2HCl . ½H₂O | 279.6° C. |
| ![C₂H₅-N tetrazinone N-(CH₂)₂] | 4-F—C₆H₄—CH₂ | H | N | base | 143.4° C. |
| (4-F—C₆H₄)₂—CH—(CH₂)₃ | (4-F—C₆H₄)₂—CH—(CH₂)₃ | H | CH | base | 171.1° C. |
| ![benzodioxane-CH₂] | C₂H₅ | H | CH | 2HNO₃ . H₂O | 266.5° C. |
| ![benzodioxane-CH₂] | C₆H₅—CH₂ | H | CH | base | 210.2° C. |

-continued

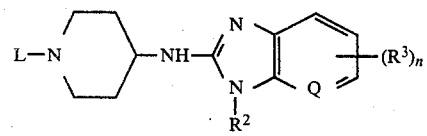

| L | R² | (R³)ₙ | Q | Base or salt form | melting point |
|---|---|---|---|---|---|
| ![oxazinone-propyl] | C₆H₅—CH₂ | H | CH | 2. HOOC—CH ‖ HOOC HC | 196.2° C. |
| C₆H₅—CH₂—CH₂ | C₆H₅—CH₂ | 5-Cl | CH | base | 126.4° C. |
| C₆H₅—NH—(CH₂)₃ | 4-F—C₆H₄—CH₂ | H | CH | base | 153.1° C. |
| C₆H₅—O—(CH₂)₃ | C₆H₅ | H | CH | base | 130.0° C. |
| C₆H₅—CH₂—CH₂ | C₆H₅ | H | CH | base | 131.0° C. |
| CH₃—(CH₂)₃ | C₆H₅ | H | CH | base | 125.3° C. |
| C₆H₅—CH=CH—CH₂ | C₆H₅ | H | CH | base | 147.1° C. |
| C₆H₅—CH₂—CH₂ | 4-F—C₆H₄ | H | CH | base | 113.8° C. |
| C₆H₅—O—(CH₂)₃ | 4-F—C₆H₄ | H | CH | base | 105.6° C. |
| 4-CH₃O—C₆H₄—S—(CH₂)₃ | 4-F—C₆H₄—CH₂ | H | CH | base | 114.5° C. |
| C₆H₅—CH₂—CH₂ | C₆H₅—CH₂ | H | N | base | 153.2° C. |
|  | 4-F—C₆H₄—CH₂ | H | CH | base | 177.6° C. |
| (dibenzocycloheptenylidene)=CH—CH₂—CH₂ |  |  |  |  |  |
| 4-(CH₃—S)—C₆H₄—(CH₂)₂ | 4-F—C₆H₄—CH₂ | H | CH | base | 176.0° C. |
| 4-(CH₃—SO₂)—C₆H₄—(CH₂)₂ | 4-F—C₆H₄—CH₂ | H | CH | ½ CH₃—CH—CH₃ OH | 235.8° C. |
| (4-F—C₆H₄)₂—CH—(CH₂)₃ | 4-F—C₆H₄—CH₂ | H | CH | base | 131.9° C. |
| CH₃—(CH₂)₃ | C₆H₅—CH₂ | H | N | base | 147.5° C. |
| C₆H₅—O—CH₂—CH₂ | C₆H₅—CH₂ | H | N | base | 142.5° C. |
| (C₆H₅)₂—CH—CH₂—CH₂ | C₅H₅—CH₂ | H | N | base | 141.4° C. |
| NC—CH₂ | 4-F—C₆H₄—CH₂ | H | CH | base | 178.7° C. |
| 4-F—C₆H₄—CO—(CH₂)₃ | 4-F—C₆H₄—CH₂ | H | N | base | 161.5° C. |
| 4-F—C₆H₄—O—(CH₂)₃ | C₆H₅—CH₂ | H | N | base | 124.9° C. |
| ![benzodioxane-methyl] | C₆H₅—CH₂ | H | N | base | 184.7° C. |
| CH₂=CH—CH₂ | C₆H₅—CH₂ | H | N | base | 132.6° C. |
| 2,6—(CH₃)₂—C₆H₃—CO—CH₂ | C₆H₅—CH₂ | H | N | base | 176.8° C. |
| ![morpholino-ethyl] O N—CH₂—CH₂ | C₆H₅—CH₂ | H | N | ½ H₂O | 153.3° C. |
| C₆H₅—CH=CH—CH₂ | C₆H₅—CH₂ | H | N | base | 124.6° C. |
| 4-F—C₆H₄—CO—(CH₂)₃ | C₆H₅—CH₂ | H | N | base | 141.0° C. |
| CH₃—(CH₃)₅ | C₆H₅—CH₂ | H | N | base | 137.3° C. |
| 3-CN-3,3—(C₆H₄)₂—C—(CH₂)₂ | 4-F—C₆H₄—CH₂ | H | N | 2 HCl.H₂O | 188.9° C. |
| 3-CN-3,3—(C₆H₄)₂—C—(CH₂)₂ | C₆H₅—CH₂ | H | CH | 2 HNO₃. H₂O | 151.1° C. |
| 3-CN-3,3—(C₆H₄)₂—C—(CH₂)₂ | CH₃—CH₂ | H | CH | 2 HNO₃. ½H₂O | 240.5° C. |

EXAMPLE XXII

A mixture of 2.4 parts of (2-bromoethyl)benzene, 6 parts of 5(6)-fluoro-1-(4-fluorophenylmethyl)-N-(4-piperidinyl)-1H-benzimidazol-2-amine dihydrobromide, 4 parts of sodium carbonate, 0.2 parts of potassium iodide and 240 parts of 4-methyl-2-pentanone is stirred and refluxed overnight using a water-separator. The reaction mixture is cooled and poured onto water. The layers are separated and the aqueous phase is extracted three times with trichloromethane. The combined organic phases are dried, filtered and evaporated. The residue is purified by column-chromatography over silica gel using a mixture of trichloromethane and methanol (97:3 by volume) as eluent. The pure fractions are collected and the eluent is evaporated. The residue is separated by column-chromatography over silica gel using a mixture of ethyl acetate and methanol (93:7 by volume) as eluent. The first fraction (A-isomer) is collected and the eluent is evaporated. The residue is washed with a mixture of 2,2'-oxybispropane and petroleumether, and dried, yielding 1 part (17.5%) of 6-fluoro-1-(4-fluorophenylmethyl)-N-[1-(2-phenylethyl)-4-piperidinyl]-1H-benzimidazol-2-amine; mp. 178.1° C.

The second fraction (B-isomer) is collected and the eluent is evaporated. The residue is washed with a mixture of 2,2'-oxybispropane and petroleumether, and dried, yielding 1.2 parts of 5-fluoro-1-(4-fluorophenylmethyl)-N-[1-(2-phenylethyl)-4-piperidinyl]-1H-benzimidazol-2-amine monohydrate; mp. 188.8° C.

EXAMPLE XXIII

A mixture of 4 parts of 1-(3-chloropropyl)-1,3-dihydro-3-(1-methylethenyl)-2H-benzimidazol-Z-one, 7 parts of 1-(phenylmethyl)-N-(4-piperidinyl)-1H-benzimidazol-2-amine dihydrobromide, 5 parts of sodium carbonate, 0.1 parts of potassium iodide and 135 parts of N,N-dimethylformamide is stirred and heated overnight at 70° C. The reaction mixture is poured onto water and the product is extracted with methylbenzene. The extract is dried, filtered and evaporated. The residue is converted into the hydrochloride salt in 2-propanol. After stirring for 1 hour, the solvent is evaporated and the residue is taken up in water. The free base is liberated in the conventional manner with ammonium hydroxide and the product is extracted with trichloromethane. The extract is dried, filtered and evaporated. The residue is crystallized from ethanol. The product is filtered off and dried, yielding 3.3 parts (45.7%) of 1,3-dihydro-1-[3-{4-[1-(phenylmethyl)-1H-benzimidazol-2-ylamino]-1-piperidinyl{propyl]-2H-benzimidazol-2-one; mp. 243.1° C.

Following the same procedure and using equivalent amounts of the appropriate starting materials there are prepared:

1-[3-{4-[1-(4-fluorophenylmethyl)-1H-benzimidazol-2-ylamino]-1-piperidinyl}propyl]-1,3-dihydro-2H-benzimidazol-2-one; mp. 237.6° C.;

1-[3-{4-[1-(4-fluorophenylmethyl)-1H-benzimidazol-2-ylamino]-3-methyl-1-piperidinyl}-propyl]-1,3-dihydro-2H-benzimidazol-2-one dihydrochloride. 2-propanolate (1:1); mp. 244.1° C.;

1-[3-{4-[3-(4-fluorophenylmethyl)-3H-imidazo[4,5-b]pyridin-2-ylamino]-1-piperidinyl}propyl]-1,3-dihydro-2H-benzimidazol-2-one; mp. 202.4° C.;

1,3-dihydro-1-{3-[4-(1-phenyl-1H-benzimidazol-2-ylamino)-1-piperidinyl]propyl}-2H-benzimidazol-2-one; mp. 185.3° C.;

1-[3-{4-[1-(4-fluorophenyl)-1H-benzimidazol-2-ylamino]-1-piperidinyl}propyl]-1,3-dihydro-2H-benzimidazol-2-one; mp. 188.9° C.; and 1,3-dihydro-1-[3-{4-[3-(phenylmethyl)-3H-imidazo[4,5-b]pyridin-2-ylamino]-1-piperidinyl}-propyl]-2H-benzimidazol-2-one; mp. 221.7° C.

EXAMPLE XXIV

A mixture of 2.3 parts of 2-(4-methoxyphenyl)ethyl methanesulfonate, 4.9 parts of 1-[(4-fluorophenyl)methyl]-N-(4-piperidinyl)-1H-benzimidazol-2-amine dihydrobromide, 3.2 parts of sodium carbonate, 0.1 parts of potassium iodide and 90 parts of N,N-dimethylformamide is stirred overnight at 70° C. The reaction mixture is poured onto water. The product is extracted with methylbenzene. The extract is washed with water, dried, filtered and evaporated. The residue is purified by column-chromatography over silica gel using a mixture of trichloromethane and methanol (98:2 by volume) as eluent. The pure fractions are collected and the eluent is evaporated. The residue is crystallized from 2,2'-oxybispropane, yielding 2.2 parts (48%) of 1-(4-fluorophenylmethyl)-N-{1-[2-(4-methoxyphenyl)ethyl]-4-piperidinyl}-1H-benzimidazol-2-amine; mp. 172.9° C.

EXAMPLE XXV

Following the procedure of Example XXIV and using equivalent amounts of the appropriate starting materials the following compounds are obtained in free base form or in the form of an acid addition salt after reacting the free base with an appropriate acid.

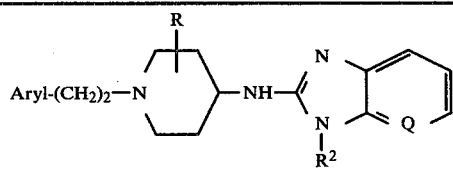

| Aryl | R | $R^2$ | Q | Base or salt form | melting point |
|---|---|---|---|---|---|
| 3,4-$(CH_3O)_2$—$C_6H_3$ | H | 4-F—$C_6H_4$—$CH_2$ | CH | base | 69.3° C. |
| 2,5-$(CH_3O_2)$—$C_6H_3$ | H | 4-F—$C_6H_4$—$CH_2$ | CH | base | 127.9° C. |
| 4-$(C_2H_5O)$—$C_6H_4$ | H | 4-F—$C_6H_4$—$CH_2$ | CH | base | 152.3° C. |
| 4-$(CH_3O)$—$C_6H_4$ | H | 4-F—$C_6H_4$—$CH_2$ | N | base | 149.1° C. |
| 3-$(CH_3O)$—$C_6H_4$ | H | 4-F—$C_6H_4$—$CH_2$ | CH | 2HCl . ½ $H_2O$ | 242.4° C. |
| 2-$(CH_3O)$—$C_6H_4$ | H | 4-F—$C_6H_4$—$CH_2$ | CH | base | 158.1° C. |
| 4-$(CH_3O)$—$C_6H_4$ | $CH_3$ | 4-F—$C_6H_4$—$CH_2$ | CH | 2HCl | 184.0° C. (cis+trans-isomer) |
| 3,4,5-$(CH_3O)_3$—$C_6H_2$ | H | 4-F—$C_6H_4$—$CH_2$ | CH | 2HCl . ½ $H_2O$ | 260.2° C. |
| 3,4-$(CH_3O)_2$—$C_6H_3$ | H | $C_6H_5$—$CH_2$ | CH | base | 149.8° C. |
| 4-$(CH_3O)$—$C_6H_4$ | $CH_3$ | $C_6H_5$—$CH_2$ | CH | 2HCl$H_2O$ | 198.4° C. (cis+trans-isomer) |
| 3-$(CH_3O)$—$C_6H_4$ | H | $C_6H_5$—$CH_2$ | CH | base | 128.6° C. |
| 4-$(C_2H_5O)$—$C_6H_4$ | H | $C_6H_5$—$CH_2$ | CH | base | 128.5° C. |

-continued

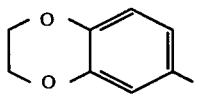

| Aryl | R | R² | Q | Base or salt form | melting point |
|---|---|---|---|---|---|
| 2-(CH₃O)—C₆H₄ | H | C₆H₅—CH₂ | CH | 2HCl . 2H₂O | 186.1° C. |
| 3-(CH₃)—C₆H₄ | H | C₆H₅—CH₂ | CH | 2HCl . H₂O | 235.7° C. |
| 4-(CH₃O)—C₆H₄ | H | C₆H₅—CH₂ | CH | 2HCl . H₂O | 274.7° C. |
| 4-Cl—C₆H₄ | H | C₆H₅—CH₂ | CH | base | 183.9° C. |
| 3,4,5-(CH₃O)₃—C₆H₂ | H | C₆H₅—CH₂ | CH | base | 156.6° C. |
| 4-(C₆H₅CH₂O)—C₆H₄ | H | 4-F—C₆H₄—CH₂ | CH | base | 155.4° C. |
| 4-CH₃O—C₆H₄ | H | C₆H₅ | CH | base | 157.8° C. |
| 4-CH₃O—C₆H₄ | H | 4-F—C₆H₄ | CH | base | 167.4° C. |
| 4-CH₃O—C₆H₄ | H | 4-NO₂—C₆H₄—CH₂ | CH | base | 200.1° C. |
| 2,4-(CH₃O)₂—C₆H₃ | H | 4-F—C₆H₄—CH₂ | CH | 2HCl . ½ H₂O | 190.4° C. |
| 4-CH₃O—C₆H₄ | H | 4-F-2-CH₃—C₆H₃—CH₂ | CH | 2HBr | 264.8° C. |
| 4-CH₃O—C₆H₄ | H | C₆H₅—CH₂ | N | base | 124.1° C. |
| 3-CH₃-4-(C₆H₅—CH₂—O)—C₆H₃ | H | 4-F—C₆H₄—CH₂ | CH | base | 145.6° C. |
| [benzodioxole] | H | 4-F—C₆H₄—CH₂ | CH | 2HCl . H₂O | 264.6° C. |

EXAMPLE XXVI

A mixture of 2.8 parts of [2-(2-thienyl)ethyl]4-methylbenzenesulfonate, 4.9 parts of 1-[4-fluorophenyl)methyl]-N-(4-piperidinyl)-1H-benzimidazol-2-amine dihydrobromide, 2.1 parts of sodium carbonate, 0.1 parts of potassium iodide and 90 parts of N,N-dimethylformamide is stirred overnight at 70° C. The reaction mixture is cooled and poured onto water. The product is extracted with methylbenzene. The extract is dried, filtered and evaporated. The residue is purified by column-chromatography over silica gel using a mixture of trichloromethane and methanol (98:2 by volume) as eluent. The pure fractions are collected and the eluent is evaporated. The residue is crystallized from 2-propanol. The product is filtered off and dried, yielding 2.3 parts (53%) of 1-(4-fluorophenylmethyl)-N-{1-[2-(2-thienyl)ethyl]-4-piperidinyl}-1H-benzimidazol-2-amine; mp. 151.6° C.

Following the same procedure and using equivalent amounts of the appropriate starting materials there are prepared:

1-(phenylmethyl)-N-{1-[2-(2-thienyl)ethyl]-4-piperidinyl}-1H-benzimidazol-2-amine dihydrochloride. monohydrate; mp. 259°–273° C.;
1-(4-fluorophenylmethyl)-N-{1-[2-(1-naphthalenyl)ethyl]-4-piperidinyl}-1H-benzimidazol-2-amine; mp. 143.1° C.; and
3-(4-fluorophenylmethyl)-N-{1-[2-(2-thienyl)ethyl]-4-piperidinyl}-3H-imidazo[4,5-b]pyridin-2-amine; mp. 176.2° C.

EXAMPLE XXVII

A mixture of 2.1 parts of 2-(ethenyl)pyridine, 3.25 parts of 1-[(4-fluorophenyl)methyl]-N-(4-piperidinyl)-1H-benzimidazol-2-amine and 80 parts of 1-butanol is stirred and refluxed overnight. The reaction mixture is evaporated. The residue is purified by column-chromatography over silica gel using a mixture of trichloromethane and methanol (97:3 by volume) as eluent. The pure fractions are collected and the eluent is evaporated. The residue is crystallized from 2,2'-oxybispropane, yielding 1 part (23%) of 1-[(4-fluorophenyl)methyl]-N-{1-[2-(2-pyridinyl)ethyl]-4-piperidinyl}-1H-benzimidazol-2-amine; mp. 133.4° C.

Following the same procedure and using equivalent amounts of the appropriate starting materials there are also prepared:

4-[1-(4-fluorophenylmethyl)-1H-benzimidazol-2-ylamino]-1-piperidinepropanenitrile; mp. 166.5° C.;
1-(4-fluorophenylmethyl)-N-{1-[2-(4-pyridinyl)ethyl]-4-piperidinyl}-1H-benzimidazol-2-amine; mp. 158.2° C.; and
3-(4-fluorophenylmethyl)-N-{1-[2-(2-pyridinyl)ethyl]-4-piperidinyl}-3H-imidazo[4,5-b]pyridin-2-amine; mp. 157.2° C.

EXAMPLE XXVIII

To 3.96 parts of 1-(4-fluorobenzoyl)aziridine, dissolved in 16 parts of benzene, are added 3.25 parts of 1-[(4-fluorophenyl)methyl]-N-(4-piperidinyl)-1H-benzimidazol-2-amine, 90 parts of benzene and 45 parts of N,N-dimethylformamide. The whole is stirred and refluxed for 5 hours. The reaction mixture is cooled and poured onto water. The layers are separated and the aqueous phase is extracted with methylbenzene. The combined organic phases are dried, filtered and evaporated. The residue is crystallized from a mixture of 2-propanone and 2,2'-oxybispropane, yielding 1part (19%) of 4-fluoro-N-[2-{4-[1-(4-fluorophenylmethyl)-1H-benzimidazol-2-ylamino]-1-piperidinyl}ethyl]benzamide; mp. 193.7° C.

Starting from 3-(phenylmethyl)-N-(4-piperidinyl)-3H-imidazo[4,5-b]pyridin-2-amine and following the same procedure there is also prepared:
4-fluoro-N-[2-{4-[3-(phenylmethyl)-3H-imidazo[4,5-b]pyridin-2-ylamino]-1-piperidinyl}ethyl]benzamide; mp. 187.5° C.

EXAMPLE XXIX

A mixture of 3.6 parts of [(4-methoxyphenoxy)methyl]oxirane, 4.9 parts of 1-[(4-fluorophenyl)methyl]-N-(4-piperidinyl)-1H-benzimidazol-2-amine dihydrobromide, 2.1 parts of sodium carbonate, 40 parts of methanol and 90 parts of benzene is stirred and refluxed overnight. The reaction mixture is filtered and the filtrate is evaporated. The residue is crystallized from a mixture of 2-propanone and 2,2'-oxybispropane. The product is filtered off and dried, yielding 2.6 parts (51%) of 4-[1-(4-fluorophenylmethyl)-1H-benzimidazol-2-ylamino]-α-(4-methoxyphenoxymethyl)-1-piperidineethanol; mp. 174.5° C.

EXAMPLE XXX

Following the procedure of Example XXIX and using equivalent amounts of the appropriate starting materials there are also prepared:
α-(phenoxymethyl)-4-{[1-(phenylmethyl)-1H-benzimidazol-2-yl]amino}-1-piperidineethanol; mp. 146.6° C.;
4-[1-(4-fluorophenylmethyl)-1H-benzimidazol-2-ylamino]-α-(phenoxymethyl)-1-piperidineethanol; mp. 181.3° C.;
4-[1-(4-fluorophenylmethyl)-1H-benzimidazol-2-ylamino]-3-methyl-α-(phenoxymethyl)-1-piperidineethanol dihydrochloride. monohydrate; mp. 163.3° C.;
α-(4-methoxyphenoxymethyl)-4-[1-(phenylmethyl)-1H-benzimidazol-2-ylamino]-1-piperidineethanol; mp. 162.7° C.;
α-(2-butoxyphenoxymethyl)-4-[1-(4-fluorophenylmethyl)-1H-benzimidazol-2-ylamino]-1-piperidineethanol; mp. 138.7° C.;
α-(2,6-dimethoxyphenoxymethyl)-4-[1-(4-fluorophenylmethyl)-1H-benzimidazol-2-ylamino]-1-piperidineethanol; mp. 140° C.;
4-[1-(3-fluorophenylmethyl)-1H-benzimidazol-2-ylamino]-α-(2-methoxyphenoxymethyl)-1-piperidineethanol; mp. 174° C.;
1-{4-[3-{4-[1-(4-fluorophenylmethyl)-1H-benzimidazol-2-ylamino]-1-piperidinyl}-2-hydroxypropoxy]-phenyl}ethanone; mp. 174.7° C.;
α-(2,6-dimethoxyphenoxymethyl)-4-[1-(phenylmethyl)-1H-benzimidazol-2-ylamino]-1-piperidineethanol; mp. 122.2° C.;
4-[1-(4-fluorophenylmethyl)-1H-benzimidazol-2-ylamino]-α-phenyl-1-piperidineethanol; mp. 184.1° C.; and
α-(phenoxymethyl)-4-[3-(phenylmethyl)-3H-imidazo[4,5-b]pyridin-2-ylamino]-1-piperidineethanol; mp. 136.6° C.

EXAMPLE XXXI

To a stirred mixture of 40.4 parts of 1-(4-fluorophenylmethyl)-N-(4-piperidinyl)-1H-benzimidazol-2-amine hydrobromide and 400 parts of methanol are added 8.8 parts of oxirane and stirring is continued overnight at room temperature. The reaction mixture is evaporated and the residue is taken up in water. The precipitated product is filtered off and dried, yielding 29 parts (64%) of 4-[1-(4-fluorophenylmethyl)-1H-benzimidazol-2-ylamino]-1-piperidineethanol monohydrobromide; mp. 248.2° C.

EXAMPLE XXXII

To 1 part of a solution of 2 parts of thiophene in 40 parts of ethanol, are added 1.5 parts of formaldehyde solution 37%, 3 parts of 1-(phenylmethyl)-N-(4-piperidinyl)-1H-benzimidazol-2-amine and 120 parts of methanol. The whole is hydrogenated at normal pressure and at room temperature with 2 parts of palladium-on-charcoal catalyst 10%. After the calculated amount of hydrogen is taken up, the catalyst is filtered off over Hyflo and the filtrate is evaporated. The residue is taken up in water and the whole is alkalized with ammonium hydroxide. The product is extracted with dichloromethane. The extract is dried, filtered and evaporated. The residue is converted into the hydrochloride salt in 2-propanol. The salt is filtered off and dried, yielding 1.5 parts (36.6%) of N-(1-methyl-4-piperidinyl)-1-(phenylmethyl)-1H-benzimidazol-2-amine dihydrochloride monohydrate; mp. 191.1° C.

Following the same procedure and using equivalent amounts of the appropriate starting materials there are also prepared:
1-(4-fluorophenylmethyl)-N-(1-methyl-4-piperidinyl)-1H-benzimidazol-2-amine; mp. 145.5° C.;
N-(1-cyclohexyl-4-piperidinyl)-1-(4-fluorophenylmethyl)-1H-benzimidazol-2-amine; mp. 168° C.;
1-(4-fluorophenylmethyl)-N-[1-(1-methyl-2-phenylethyl)-4-piperidinyl]-1H-benzimidazol-2-amine; mp. 182.4° C.;
1-methyl-N-(1-methyl-4-piperidinyl)-1H-benzimidazol-2-amine dihydrochloride dihydrate; 300.6° C.;
1-ethyl-N-[1-methylethyl)-4-piperidinyl]-1H-benzimidazol-2-amine; mp. 156.6° C.
N-(1-methyl-4-piperidinyl)-1-phenyl-1H-benzimidazol-2-amine; mp. 128.5° C.
3-(4-fluorophenylmethyl)-N-(1-methyl-4-piperidinyl)-3H-imidazo[4,5-b]pyridin-2-amine; mp. 153.4° C.; and
N-(1-methyl-4-piperidinyl)-3-(phenylmethyl)-3H-imidazo[4,5-b]pyridin-2-amine; mp. 141.4° C.

EXAMPLE XXXIII

To 1 part of a solution of 2 parts of thiophene in 40 parts of ethanol, are added 2 parts of cyclohexanone, 3 parts of 1-(phenylmethyl)-N-(4-piperidinyl)-1H-benzimidazol-2-amine, 1 part of acetic acid and 120 parts of methanol. The whole is hydrogenated at normal pressure and at room temperature with 2 parts of palladium-on-charcoal catalyst 10%. After the calculated amount of hydrogen is taken up, the catalyst is filtered off over Hyflo and the filtrate is evaporated. The residue is taken up in water and the whole is alkalized with sodium hydroxide. The product is extracted with tetrahydrofuran. The extract is dried, filtered and evaporated. The residue is crystallized from a mixture of 2,2'-oxybispropane and 2-propanol, yielding 1.5 parts (38.5%) of N-(1-cyclohexyl-4-piperidinyl)-1-(phenylmethyl)-1H-benzimidazol-2-amine; amine; mp. 143° C.

Following the same procedure and using equivalent amounts of the appropriate starting materials there are also prepared:
1-phenyl-4-{4-[1-(phenylmethyl)-1H-benzimidazol-2-ylamino]-1-piperidinyl}cyclohexanecarbonitrile; mp. 106°–107° C.;
4-{4-[1-(4-fluorophenylmethyl)-1H-benzimidazol-2-ylamino]-1-piperidinyl}-1-phenylcyclohexanecarbonitrile dihydrochloride; mp. 275° C.;

1-[3-{4-[1-(4-fluorophenylmethyl)-1H-benzimidazol-2-ylamino]-1-piperidinyl}butyl]-1,3-dihydro-2H-benzimidazol-2-one; mp. 234.8° C.;
N-(1-cyclohexyl-4-piperidinyl)-3-(phenylmethyl)-3H-imidazo[4,5-b]pyridin-2-amine; mp. 129.2° C.;
N-[1-(1-methylethyl)-4-piperidinyl]-3-(phenylmethyl)-3H-imidazo[4,5-b]pyridin-2-amine; mp. 136.4° C.; and
1-(4-fluorophenylmethyl)-N-[1-{2-[(phenylmethyl)amino]ethyl}-4-piperidine]-1H-benzimidazol-2-amine; mp. 135.6° C.

EXAMPLE XXXIV

A mixture of 39.8 parts of N-(2-aminophenyl)-N'-ethyl-N'-[I-(2-phenylethyl)-4-piperidinyl]thiourea, 15 parts of mercury oxide, 0.1 parts of sulfur and 400 parts of methanol is stirred and refluxed overnight. The reaction mixture is filtered hot over Hyflo and the filtrate is evaporated. The residue is crystallized from 4-methyl-2-pentanone. The product is filtered off and dried, yielding 14.5 parts (43%) of N-ethyl-N-[I-(2-phenylethyl)-4-piperidinyl]-1H-benzimidazol-2-amine; mp. 204.9° C.

Following the same procedure and using equivalent amounts of the appropriate starting materials there are also prepared:
N-[1-(2-phenylethyl)-4-piperidinyl]-N-propyl-1H-benzimidazol-2-amine;
N-(1-methylethyl)-N-[1-(2-phenylethyl)-4-piperidinyl]-1H-benzimidazol-2-amine; mp. 228.4° C.;
N-cyclopropyl-N-[1-(2-phenylethyl)-4-piperidinyl]-1H-benzimidazol-2-amine; mp. 193.5° C.;
N-[1-(2-phenylethyl)-4-piperidinyl]-N-(phenylmethyl)-1H-benzimidazol-2-amine; mp. 191.5° C.

EXAMPLE XXXV

To a stirred and cooled (below 5° C.) mixture of 3.3 parts of N-methyl-N-[1-(2-phenylethyl)-4-piperidinyl]-1H-benzimidazol-2-amine, 100 parts of dimethylsulfoxide and 90 parts of benzene are added 0.5 parts of sodium hydride dispersion 50%. After stirring for 30 minutes, 1.5 parts of 1-(chloromethyl)-4-fluorobenzene are added and stirring is continued overnight while the mixture is allowed to reach room temperature. The reaction mixture is poured onto water and the product is extracted with methylbenzene. The extract is dried, filtered and evaporated. The residue is converted into the hydrochloride salt in 2-propanone. The salt is filtered off and crystallized from 2-propanol, yielding 2.8 parts (54.4%) of 1-[(4-fluorophenyl)methyl]-N-methyl-N-[1-(2-phenylethyl)-4-piperidinyl]-1H-benzimidazol-2-amine dihydrochloride; mp. 246.6° C.

Following the same procedure and using equivalent amounts of the appropriate starting materials there are also prepared:
1-[(4-chlorophenyl)methyl]-N-[1-(2-phenylethyl)-4-piperidinyl]-N-(phenylmethyl)-1H-benzimidazol-2-amine; mp. 138° C.;
1-[(2-methoxyphenyl)methyl]-N-[1-(2-phenylethyl)-4-piperidinyl]-N-(phenylmethyl)-1H-benzimidazol-2-amine; mp. 148.3° C.;
1-[(4-methoxyphenyl)methyl]-N[1-(2-phenylethyl)-4-piperidinyl]-N-(phenylmethyl)-1H-benzimidazol-2-amine; mp. 122.4° C.;
1-[(4-fluorophenyl)methyl]-N-[1-(2-phenylethyl)-4-piperidinyl]-N-(phenylmethyl)-1H-benzimidazol-2-amine; mp. 108.5° C.;
1-(4-bromophenylmethyl)-N-[1-(2-phenylethyl)-4-piperidinyl]-N-(phenylmethyl)-1H-benzimidazol-2-amine; mp. 139.3° C.;
1-[(4-methylphenyl)methyl]-N-[1-(2-phenylethyl)-4-piperidinyl]-N-(phenylmethyl)-1H-benzimidazol-2-amine; mp. 123.4° C.;
1-(2-chlorophenylmethyl)-N-[1-(2-phenylethyl)-4-piperidinyl]-N-(phenylmethyl)-1H-benzimidazol-2-amine; mp. 105.5° C.;
1-butyl-N-[1-(2-phenylethyl)-4-piperidinyl]-N-(phenylmethyl)-1H-benzimidazol-2-amine; mp. 76.5° C.; and
1-ethyl-N-[1-(2-phenylethyl)-4-piperidinyl]-N-(phenylmethyl)-1H-benzimidazol-2-amine dihydrochloride. dihydrate; mp. 157.2° C.

EXAMPLE XXXVI

A mixture of 1.6 parts of 1-(1-chloroethyl)-4-fluorobenzene, 3.2 parts of N-[1-(2-phenylethyl)-4-piperidinyl]-1H-benzimidazol-2-amine, 1 part of sodium carbonate, 0.1 parts of potassium iodide and 120 parts of 4-methyl-2-pentanone is stirred and refluxed overnight with water-separator. The reaction mixture is cooled, poured onto water and the layers are separated. The organic phase is dried, filtered and evaporated. The residue is purified by column-chromatography over silica gel using a mixture of trichloromethane and methanol (98:2 by volume) as eluent. The pure fractions are collected and the eluent is evaporated. The residue is crystallized from 2,2'-oxybispropane. The product is filtered off and dried, yielding 1.8 parts (40.7%) of 1-[1-(4-fluorophenyl)ethyl]-N-[1-(2-phenylethyl)-4-piperidinyl]-1H-benzimidazol-2-amine; mp. 161.7° C.

EXAMPLE XXXVII

Following the procedures of Examples XXXV and XXXVI and using equivalent amounts of the appropriate starting materials the following compounds are obtained in free base form or in the form of an acid addition salt after reacting the free base with an appropriate acid

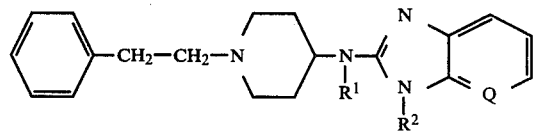

| $R^1$ | $R^2$ | Base or Salt form | melting point |
|---|---|---|---|
| H | $C_6H_5-(CH_2)_2$ | base | 136.1° C. |
| H | $4\text{-}F\text{-}C_6H_4\text{-}(CH_2)_2$ | base | 151.5° C. |
| H | $(4\text{-}F\text{-}C_6H_5)\text{-}CH(C_6H_5)$ | 2HCl . $H_2O$ | 239.6° C. |
| H | $C_6H_5\text{-}CH(CH_3)\text{-}CH_2$ | base | 144.5° C. |
| H | ![pyridyl-CH2] | base | 127.6° C. |
| H | $C_6H_5\text{-}CH(CH_3)$ | 2HCl . $H_2O$ | 239.9° C. |
| H | $(4\text{-}F\text{-}C_6H_4)_2CH$ | base | 172.5° C. |
| H | $2\text{-}(CH_3O)\text{-}C_6H_4\text{-}CH_2$ | base | 128.5° C. |
| $CH_3$ | $2\text{-}(CH_3O)\text{-}C_6H_4\text{-}CH_2$ | $2HNO_3$ | 169.7° C. |
| $CH_3$ | $2\text{-}Cl\text{-}C_6H_4\text{-}CH_2$ | 2HCl | 251.2° C. |
| $CH_3$ | $4\text{-}Br\text{-}C_6H_4\text{-}CH_2$ | 2HCl . $H_2O$ | 187.1° C. |
| $CH_3$ | $4\text{-}(CH_3O)\text{-}C_6H_4\text{-}CH_2$ | $2HNO_3$ | 163.5° C. |
| $CH_3$ | $C_6H_5\text{-}CH_2$ | 2HCl | 243.1° C. |
| $CH_3$ | $4\text{-}(CH_3)\text{-}C_6H_4\text{-}CH_2$ | $2HNO_3$ | 175.3° C. |
| $CH_3$ | $4\text{-}Cl\text{-}C_6H_4\text{-}CH_2$ | 2HCl | 251.3° C. |
| $CH_3$ | n. $C_4H_9$ | 2HCl | 257.9° C. |
| $CH_3$ | $C_2H_5$ | 2HCl . $H_2O$ | 243.1° C. |
| $C_2H_5$ | $C_6H_5\text{-}CH_2$ | base | 115.8° C. |
| $C_2H_5$ | $C_2H_5$ | base | 93.2° C. |
| $nC_3H_7$ | $C_6H_5\text{-}CH_2$ | 2HCl . $H_2O$ | 159.4° C. |
| $nC_3H_7$ | $nC_4H_9$ | $(COOH)_2$ | 177.5° C. |
| $nC_3H_7$ | $C_2H_5$ | 2HCl | 160.7° C. |

-continued

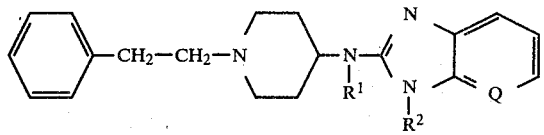

| R¹ | R² | Base or Salt form | melting point |
|---|---|---|---|
| iC₃H₇ | C₂H₅ | 2HCl . ½ H₂O | 206.8° C. |
| iC₃H₇ | C₆H₅—CH₂ | (COOH)₂ | 215.6° C. |
| iC₃H₇ | nC₄H₉ | (COOH)₂ | 198.0° C. |
| nC₄H₉ | C₆H₅—CH₂ | 2HCl . 2H₂O | 160.0° C. |
| nC₄H₉ | 4-Br—C₆H₄—CH₂ | 2HCl . 2H₂O | 137.2° C. |
| nC₄H₉ | nC₄H₉ | 2HCl . 2H₂O | 138.7° C. |
| nC₄H₉ | 4-F—C₆H₄—CH₂ | 2HCl . 2H₂O | 135.5° C. |
|  | C₂H₅ | 2HCl . 2H₂O | 123.8° C. |

EXAMPLE XXXVIII

A mixture of 3.2 parts of N-[1-(2-phenylethyl)-4-piperidinyl]-1H-benzimidazol-2-amine, 2.9 parts of [2-(2-thienyl)ethyl] 4-methylbenzenesulfonate, 1 part of sodium carbonate and 135 parts of 4-methyl-2-pentanone is stirred and refluxed overnight with water-separator. The reaction mixture is poured onto water and the layers are separated. The organic phase is dried, filtered and evaporated. The residue is purified by column-chromatography over silica gel using a mixture of trichloromethane and methanol (98:2 by volume) as eluent. The pure fractions are collected and the eluent is evaporated. The residue is crystallized from a mixture of 2,2'-oxybispropane and 2-propanone, yielding 1 part (23.2%) of N-[1-(2-phenylethyl)-4-piperidinyl]-1-[2-(2-thienyl)ethyl]-1H-benzimidazol-2-amine; mp. 118.3° C.

EXAMPLE XXXIX

To a stirred and cooled (below 5° C.) mixture of 4 parts of N-[1-(2-phenylethyl)-4-piperidinyl]-1-(phenylmethyl)-1H-benzimidazol-2-amine, 100 parts of dimethyl sulfoxide and 90 parts of benzene are added 0.5 parts of sodium hydride dispersion 50%. After stirring for 30 minutes at a temperature below 5° C., 1.3 parts of (chloromethyl)benzene are added and stirring is continued for 4 hours while the mixture is allowed to reach room temperature. The reaction mixture is poured onto water and the product is extracted with methylbenzene. The extract is dried, filtered and evaporated. The residue is purified by column-chromatography over silica gel using a mixture of trichloromethane and methanol (97:3 by volume) as eluent. The pure fractions are collected and the eluent is evaporated. The residue is converted into the nitrate salt in 2-propanone. The salt is filtered off and dried, yielding 1.5 parts (24%) of N-[1-(2-phenylethyl)-4-piperidinyl-N,1-bis(phenylmethyl)-1H-benzimidazol-2-amine dinitrate; mp. 156.9° C.

EXAMPLE XL

To 1 part of a solution of 2 parts of thiophene in 40 parts of ethanol are added 3.3 parts of 1-(4-fluorophenylmethyl)-N-{1-[2-(4-nitrophenyl)ethyl]-4-piperidinyl}-1H-benzimidazol-2-amine and 120 parts of methanol. The whole is hydrogenated at normal pressure and at room temperature with 2 parts of platinum-on-charcoal catalyst 5%. After the calculated amount of hydrogen is taken up, the catalyst is filtered off and the filtrate is evaporated. The residue is purified by column-chromatography over silica gel using a mixture of methylbenzene and methanol (95:5 by volume) saturated with ammonia, as eluent. The pure fractions are collected and the eluent is evaporated. The residue is crystallized from 2-propanol, yielding 1.3 parts (42%) of N-{1-[2-(4-aminophenyl)ethyl]-4-piperidinyl}-1-(4-fluorophenylmethyl)-1H-benzimidazol-2-amine; mp. 195.4° C.

Following the same hydrogenation procedure and starting from the corresponding nitro-compound there is also prepared:

1-[(4-aminophenyl)methyl]-N-{1-[2-(4-methoxyphenyl)ethyl]-4-piperidinyl}-1H-benzimidazol-2-amine monohydrate; mp. 142.6° C.

EXAMPLE XLI

A mixture of 7.5 parts of 1-(4-fluorophenylmethyl)-N-[1-{2-[4-(phenylmethoxy)phenyl]ethyl}-4-piperidinyl]-1H-benzimidazol-2-amine and 120 parts of methanol is hydrogenated at normal pressure and at room temperature with 2 parts of palladium-on-charcoal catalyst 10%. After the calculated amount of hydrogen is taken up, the catalyst is filtered off and the filtrate is evaporated. The residue is suspended in 2,2'-oxybispropane. The product is filtered off and dried, yielding 5.5 parts (88.5%) of 4-[2-{4-[1-(4-fluorophenylmethyl)-1H-benzimidazol-2-ylamino]-1-piperidinyl}ethyl]phenol hemihydrate; mp. 111.6° C.

Following the same hydrogenation procedure and starting from 1-(4-fluorophenylmethyl)-N-[1-{2-[3-methyl-4-(phenylmethoxy)phenyl]ethyl}-4-piperidinyl]-1H-benzimidazol-2-amine there is also prepared 4-{2-[4-{[1-(4-fluorophenylmethyl)-1H-benzimidazol-2-yl]amino}-1-piperidinyl]ethyl}-2-methylphenol dihydrochloride monohydrate; mp. 277.8° C.

A mixture of 8 parts of 1-(4-fluorophenylmethyl)-N-{1-[2-(3-methoxyphenyl)ethyl]-4-piperidinyl}-1H-benzimidazol-2-amine and 225 parts of a hydrobromic acid solution 48% in acetic acid is stirred and refluxed for 3 hours. The reaction mixture is evaporated and the residue is taken up in water. The free base is liberated in the conventional manner with ammonium hydroxide and extracted with trichloromethane. The extract is dried, filtered and evaporated. The residue is purified twice by column-chromatography over silica gel using first a mixture of trichloromethane and methanol (98:2 by volume) and then a mixture of trichloromethane and methanol (95:5 by volume) as eluent. The pure fractions are collected and the eluent is evaporated. The residue is converted into the hydrochloride salt in 2-propanone. The salt is filtered off and dried, yielding 0.8 parts (9%) of 3-[2-{4-[1-(4-fluorophenylmethyl)-1H-benzimidazol-2-yl-amino]-1-piperidinyl}ethyl]phenol dihydrochloride. monohydrate; mp. 209.8° C.

EXAMPLE XLII

A mixture of 1.2 parts of 3-bromo-1-propene, 4 parts of 4-[2-{4-[1-(4-fluorophenylmethyl)-1H-benzimidazol-2-ylamino]-1-piperidinyl}ethyl]phenol, 1.4 parts of potassium carbonate and 160 parts of 2-propanone is stirred and refluxed overnight. The reaction mixture is filtered and the filtrate is evaporated. The residue is purified by column-chromatography over silica gel using a mixture of trichloromethane and methanol (98:2 by volume) as eluent. The pure fractions are collected and the eluent is evaporated. The residue is converted into the hydrochloride salt in 2-propanone. The salt is filtered off and dried, yielding 1 part (19.9%) of 1-(4-fluorophenylmethyl)-N-[1-{2-[4-(2-propenyloxy)-phenyl]ethyl}-4-piperidinyl]-1H-benzimidazo 1-2-amine dihydrochloride; mp. 224.7° C.

EXAMPLE XLIII

A mixture of 15 parts of thionyl chloride, 4 parts of 4-[1-(4-fluorophenylmethyl)-1H-benzimidazol-2-ylamino]-1-piperidineethanol dihydrochloride and 375 parts of trichloromethane is stirred and refluxed overnight. The precipitated product is filtered off and dried, yielding 13 parts (83%) of N-[1-(2-chloroethyl)-4-piperidinyl]-1-(4-fluorophenylmethyl)-1H-benzimidazol-2-amine dihydrochloride; mp. >260° C.

EXAMPLE XLIV

A mixture of 0.9 parts of morpholine, 4.8 parts of N-[1-(2-chloroethyl)-4-piperidinyl]-1-(4-fluorophenylmethyl)-1H-benzimidazol-2-amine dihydrochloride, 3 parts of sodium carbonate, 0.1 parts of potassium iodide and 135 parts of N,N-dimethylformamide is stirred and heated overnight at 70° C. The reaction mixture is poured onto water and the product is extracted with methylbenzene. The extract is dried, filtered and evaporated. The residue is purified by column-chromatography over silica gel using a mixture of trichloromethane and methanol (98:2 by volume) as eluent. The pure fractions are collected and the eluent is evaporated. The residue is crystallized from a mixture of 2-propanone and 2,2'-oxybispropane, yielding 0.6 parts (12.5%) of [2-{4-[1-(4-fluorophenylmethyl)-1H-benzimidazol-2-ylamino]-1-piperidinyl}ethyl] 4-morpholinecarboxylate; mp. 144.8° C.

EXAMPLE XLV

A mixture of 3.6 parts of morpholine, 4.8 parts of N-[1-(2-chloroethyl)-4-piperidinyl]-1-(4-fluorophenylmethyl)-1H-benzimidazol-2-amine dihydrochloride, 0.1 parts of potassium iodide and 135 parts of N,N-dimethylformamide is stirred and heated overnight at 70° C. The reaction mixture is poured onto water and the product is extracted with methylbenzene. The extract is dried, filtered and evaporated. The residue is converted into the hydrochloride salt in methanol. The salt is filtered off and dried, yielding 1 part (18.3%) of 1-(4-fluorophenylmethyl)-N-{1-[2-(4-morpholinyl)ethyl]-4-piperidinyl}-1H-benzimidazol-2-amine trihydrochloride; mp.+300° C.

EXAMPLE XLVI

To a stirred mixture of 4.5 parts of 4-[1-(4-fluorophenylmethyl)-1H-benzimidazol-2-ylamino]-1-piperidineethanol, 2 parts of N,N-diethylethanamine and 195 parts of dichloromethane is added dropwise a solution of 1.7 parts of 4-methoxybenzoyl chloride in dichloromethane. Upon completion, stirring is continued overnight at room temperature. Water is added and the layers are separated. The organic phase is dried, filtered and evaporated. The residue is purified by column-chromatography over silica gel using a mixture of trichloromethane and methanol (98:2 by volume) as eluent. The pure fractions are collected and the eluent is evaporated. The residue is converted into the hydrochloride salt in 2-propanone. The salt is filtered off and dried, yielding 2.5 parts (43.5%) of [2-{4-[1-(4-fluorophenylmethyl)-1H-benzimidazol-2-ylamino]-1-piperidinyl}ethyl] 4-methoxybenzoate; dihydrochloride. hemihydrate; mp. 189.2° C.

Following the same procedure and using equivalent amounts of the appropriate starting materials there are also prepared:
{4-[2-{4-[1-(4-fluorophenylmethyl)-1H-benzimidazol-2-ylamino]-1-piperidinyl}ethyl]phenyl}benzeneacetate; mp. 135.1° C.;
{4-[2-{4-[1-(4-fluorophenylmethyl)-1H-benzimidazol-2-ylamino]-1-piperidinyl}ethyl]phenyl}4-methoxybenzoate; mp. 157.1° C.;
{4-[2-{4-[1-(4-fluorophenylmethyl)-1H-benzimidazol-2-ylamino]-1-piperidinyl}ethyl]phenyl}methyl carbonate; mp. 134.5° C.; and
{4-[2-{4-[1-(4-fluorophenylmethyl)-1H-benzimidazol-2-ylamino]-1-piperidinyl}ethyl]phenyl}(phenylmethyl) carbonate; mp. 147.8° C.

EXAMPLE XLVII

A mixture of 1.2 parts of chloroacetonitrile, 6.7 parts of 4-[2-{4-[1-(4-fluorophenylmethyl)-1H-benzimidazol-2-ylamino]-1-piperidinyl}ethyl]phenol, 2.8 parts of potassium carbonate and 160 parts of 2-propanone is stirred and refluxed overnight. The reaction mixture is poured onto water and the product is extracted with methylbenzene. The extract is dried, filtered and evaporated. The residue is converted into the hydrochloride salt in 2-propanone. The salt is filtered off and dried, yielding 7.4 parts (78.6%) of {4-[2-{4-[1-(4-fluorophenylmethyl)-1H-benzimidazol-2-ylamino]-1-piperidinyl}ethyl]phenoxy}acetonitrile dihydrochloride. monohydrate; mp. 224.6° C.

Following the same procedure and using equivalent amounts of the appropriate starting materials there are prepared:
ethyl 2-{4-[2-{4-[1-(4-fluorophenylmethyl)-1H-benzimidazol-2-ylamino]-1-piperidinyl}ethyl]phenoxy}acetate; mp. 109.1° C.;
methyl 2-{4-[2-{4-[1-(4-fluorophenylmethyl)-1H-benzimidazol-2-ylamino]-1-piperidinyl}ethyl]phenoxy}acetate; mp. 109.8° C.; and
1-[2-{4-[2-{4-[1-(4-fluorophenylmethyl)-1H-benzimidazol-2-ylamino]-1-piperidinyl}ethyl]phenoxy}acetyl]piperidine dihydrochloride; mp. 247° C.

EXAMPLE XLVIII

A mixture of 0.5 parts of isocyanatomethane, 4.5 parts of 4-[2-{4-[1-(4-fluorophenylmethyl)-1H-benzimidazol-2-ylamino]-1-piperidinyl}ethyl]phenol and 135 parts of tetrahydrofuran is stirred overnight at room temperature. The reaction mixture is evaporated. The residue is purified by column-chromatography over silica gel using a mixture of trichloromethane and methanol (98:2 by volume) as eluent. The pure fractions are collected and the eluent is evaporated. The residue is crystallized from a mixture of 2-propanone and 2,2'-oxybispropane, yielding 1 part (20%) of {4-[2-{4-[1-(4-fluorophenylmethyl)-1H-benzimidazol-2-ylamino]-1-piperidinyl}ethyl]phenyl}methylcarbamate; mp. 172.2° C.

By the addition-reaction of 4-[2-{4-[1-(4-fluorophenylmethyl)-1H-benzimidazol-2-ylamino]-1-piperidinyl}ethyl]phenol to 1-isocyanatobutane there is also repared: {4-[2-{4-[1-(4-fluorophenylmethyl)-1H-benzimidazol-2-ylamino]-1-piperidinyl}ethyl]phenyl}-butyl carbamate; mp. 142.5° C.

EXAMPLE IL

A mixture of 9 parts of 4-[1-(4-fluorophenylmethyl)-1H-benzimidazol-2-ylamino]-1-piperidineacetonitrile and 200 parts of methanol, saturated with ammonia, is hydrogenated at normal pressure and at room temperature with 3 parts of Raney-nickel catalyst. After the calculated amount of hydrogen is taken up, the catalyst is filtered off and the filtrate is evaporated. The residue is converted into the hydrochloride salt in 2-propanone. The salt is filtered off and crystallized from a mixture of 2-propanone and methanol, yielding 11 part of N-[1-(2-aminoethyl)-4-piperidinyl]-1-(4-fluorophenylmethyl)-1H-benzimidazol-2-amine trihydrochloride; mp. 292.9° C.

Following the same hydrogenation procedure and starting from 4-[1-(4-fluorophenylmethyl)-1H-benzimidazol-2-ylamino]-1-piperidinepropanenitrile there is also prepared: N-[1-(3-aminopropyl)-4-piperidinyl]-1-(4-fluorophenylmethyl)-1H-benzimidazol-2-amine trihydrochloride. monohydrate; mp. 239.3° C.

EXAMPLE L

A mixture of 1.8 parts of 1-isothiocyanato-2-nitrobenzene, 3.7 parts of N-[1-(2-aminoethyl)-4-piperidinyl]-1-(4-fluorophenylmethyl)-1H-benzimidazol-2-amine and 135 parts of tetrahydrofuran is stirred overnight at room temperature. The reaction mixture is evaporated. The residue is purified by column-chromatography over silica gel using a mixture of trichloromethane and methanol (98:2 by volume) as eluent. The pure fractions are collected and the eluent is evaporated, yielding 3.7 parts (67%) of N-[2-{4-[1-(4-fluorophenylmethyl)-1H-benzimidazol-2-ylamino]-1-piperidinyl}ethyl]-N'-(2-nitrophenyl)thiourea as a residue.

A mixture of 3.7 parts of N-[2-{4-[1-(4-fluorophenylmethyl)-1H-benzimidazol-2-ylamino]-1-piperidinyl}ethyl]-N'-(2-nitrophenyl)thiourea, 7 parts of iron-powder, 0.25 parts of concentrated hydrochloric acid, 48 parts of ethanol and 15 parts of water is stirred and refluxed for 1 hour. The reaction mixture is alkalized with methanol saturated with ammonia. The whole is filtered and the filtrate is evaporated, yielding 3.5 parts of N-(2-aminophenyl)-N'-[2-{4-[1-(4-fluorophenylmethyl)-1H-benzimidazol-2-ylamino]-1-piperidinyl}ethyl]thiourea as a residue.

A mixture of 3.5 parts of N-(2-aminophenyl)-N'-[2-}4-[1-(4-fluorophenylmethyl)-1H-benzimidazol-2-ylamino]-1-piperidinyl}ethyl]thiourea, 2.2 parts of mercury (II) oxide, 0.1 parts of sulfur and 80 parts of ethanol is stirred and refluxed for 1 hour. The reaction mixture is filtered over Hyflo and the filtrate is evaporated. The residue is purified by column-chromatography over silica gel using a mixture of trichloromethane and methanol (95:5 by volume) as eluent. The pure fractions are collected and the eluent is evaporated. The residue is crystallized from 2-propanone, yielding 1.5 parts (44.4%) of N-{1-[2-(1H-benzimidazol-2-ylamino)ethyl]-4-piperidinyl}-1-(4-fluorophenylmethyl)-1H-benzimidazol-2-amine; mp. 253.4° C.

EXAMPLE LI

A solution of 4.77 parts of N-[1-(2-aminoethyl)-4-piperidinyl]-1-(4-fluorophenylmethyl)-1H-benzimidazol-2-amine trihydrochloride in methanol saturated with ammonia is stirred for 1 hour at room temperature. The solvent is evaporated and the residue is taken up in 135 parts of tetrahydrofuran. Then there are added 6 parts of isocyanatomethane and the whole is stirred overnight at room temperature. The precipitated product is filtered off and dried, yielding 3 parts (70.7%) of N-[2-{4-[1-(4-fluorophenylmethyl)-1H-benzimidazol-2-ylamino]-1-piperidinyl}ethyl]-N'-methylurea. hemihydrate; mp. 231.4° C.

EXAMPLE LII

To a stirred mixture of 3.8 parts of N-[1-(2-aminoethyl)-4-piperidinyl]-1-(4-fluorophenylmethyl)-1H-benzimidazol-2-amine, 1 part of N,N-diethylethanamine and 195 parts of dichloromethane is added dropwise a solution of 1.7 parts of 4-methoxybenzoyl chloride in dichloromethane. Upon completion, stirring is continued overnight at room temperature. The reaction mixture is poured onto water and the layers are separated. The organic phase is dried, filtered and evaporated. The residue is purified by column-chromatography over silica gel using a mixture of trichloromethane and methanol (98:2 by volume) as eluent. The pure fractions are collected and the eluent is evaporated. The residue is converted into the hydrochloride salt in 2-propanol. The salt is filtered off and dried, yielding 1 part of N-[2-{4-[1-(4-fluorophenylmethyl)-1H-benzimidazol-2-ylamino]-1-piperidinyl}ethyl]-4-methoxy-N-(4-methoxybenzoyl)benzamide dihydrochloride. dihydrate; mp. 161.5° C.

EXAMPLE LIII

To 1 part of a solution of 2 parts of thiophene in 40 parts of ethanol are added 1 part of paraformaldehyde, 3.5 parts of N-[1-(2-aminoethyl)-4-piperidinyl]-1-(4-fluorophenylmethyl)-1H-benzimidazol-2-amine and 120 parts of methanol. The whole is hydrogenated at normal pressure and at room temperature with 2 parts of palladium-on-charcoal catalyst 10%. After the calculated amount of hydrogen is taken up, the catalyst is filtered off and the filtrate is evaporated. The residue is taken up in water and the product is extracted with trichloromethane. The extract is dried, filtered and evaporated. The residue is crystallized from a mixture of 2-propanone and 2,2'-oxybispropane, yielding 1.5 parts (42%) of N-{1-[2-(dimethylamino)ethyl]-4-piperidinyl}-1-(4-fluorophenylmethyl)-1H-benzimidazol-2-amine; mp. 166.1° C.

EXAMPLE LIV

To 1 part of a solution of 2 parts of thiophene in 40 parts of ethanol are added 2.5 parts of benzaldehyde, 3.7 parts of N-[1-(2-aminoethyl)-4-piperidinyl]-1-(4-fluorophenylmethyl)-1H-benzimidazol-2-amine and 120 parts of methanol. The whole is hydrogenated at normal pressure and at room temperature with 2 parts of palladium-on-charcoal catalyst 10%. After the calculated amount of hydrogen is taken up, the catalyst is filtered off over hyflo and the filtrate is evaporated. The residue is converted into the hydrochloride salt in 2-propanone. The salt is filtered off and taken up in water. The free base is liberated in the conventional manner with ammonium hydroxide and extracted with dichloromethane. The extract is dried, filtered and evaporated. The residue is crystallized from a mixture of 2-propanone and 2,2'-oxybispropane, yielding 1.5 parts (27.5%) of N-[1-{2-[bis(phenylmethyl)amino]ethyl}-4-piperidinyl]-1-(4-fluorophenylmethyl)-1H-benzimidazol-2-amine; mp. 116.4° C.

EXAMPLE LV

A mixture of 5.5 parts of N-[1-(1H-benzimidazol-2-yl)-4-piperidinyl]-1-(phenylmethyl)-1H-benzimidazol-2-amine dinitrate, 1.5 parts of 1-(chloromethyl)-4-fluorobenzene, 5 parts of sodium carbonate, 0.1 parts of potassium iodide and 120 parts of 4-methyl-2-pentanone is stirred and refluxed overnight using a water-separator. The reaction mixture is poured onto water and the layers are separated. The organic phase is dried, filtered and evaporated. The residue is purified by column-chromatography over silica gel using a mixture of trichloromethane and methanol (98:2 by volume) as eluent. The pure fractions are collected and the eluent is evaporated. The residue is crystallized from a mixture of 4-methyl-2-pentanone and 2,2'-oxybispropane. The product is filtered off and dried, yielding 1.5 parts (28.3%) of N-{1-[1-(4-fluorophenylmethyl)-1H-benzimidazol-2-yl]-4-piperidinyl}-1-(phenylmethyl)-1H-benzimidazol-2-amine; mp. 163.9° C.

EXAMPLE LVI

A mixture of 3.7 parts of 1-(4-fluorophenylmethyl)-N-{1-[3-(4-methoxyphenylthio)propyl]-4-piperidinyl}-1H-benzimidazol-2-amine, 2.42 parts of hydrogen peroxide solution 30% and 20 parts of acetic acid is stirred and refluxed for 1 hour. The reaction mixture is cooled and poured onto ice-water. The whole is alkalized with sodium hydroxide solution 50% and the product is extracted with trichloromethane. The extract is washed with water, dried, filtered and evaporated. The residue is purified by column-chromatography over silica gel using a mixture of trichloromethane and methanol (98:2 by volume) as eluent. The pure fractions are collected and the eluent is evaporated. The residue is converted into the ethanedioate salt in methanol and 2-propanol. The salt is filtered off and dried, yielding 0.8 parts (16%) of 1-(4-fluorophenylmethyl)-N-{1-[3-(4-methoxyphenylsulfonyl)propyl]-4-piperidinyl}-1H-benzimidazol-2-amine ethanedioate (1:2); mp. 213.1° C.

EXAMPLE LVII

A mixture of 5 parts of ethyl 2-{4-[2-{4-[1-(4-fluorophenylmethyl)-1H-benzimidazol-2-ylamino]-1-piperidinyl}ethyl]phenoxy}acetate, 70 parts of ethanamine solution 50% and 40 parts of methanol is stirred for 3 hours at room temperature. The reaction mixture is evaporated and the residue is crystallized twice from 2-propanol, yielding 1 part (19%) of N-ethyl-2-{4-[2-{4-[1-(4-fluorophenylmethyl-1H-benzimidazol-2-ylamino]-1-piperidinyl}ethyl]phenoxy}acetamide; mp. 160.9° C.

EXAMPLE LVIII

A mixture of 3.5 parts of methyl 2-{4-[2-{4-[1-(4-fluorophenylmethyl)-1H-benzimidazol-2-ylamino]-1-piperidinyl}ethyl]phenoxy acetate, 90 parts of concentrated ammonium hydroxide and 40 parts of methanol is stirred for 4 hours at room temperature. The reaction mixture is evaporated. The residue is purified by column-chromatography over silica gel using a mixture of trichloromethane and methanol (95:5 by volume) as eluent. The pure fractions are collected and the eluent is evaporated. The residue is crystallized from 2-propanol, yielding 1 part (28.5%) of 2-{4-[2-{4-[1-(4-fluorophenylmethyl)-1H-benzimidazol-2-ylamino]-1-piperidinyl}ethyl]-phenoxy}acetamide; mp. 180.4° C.

EXAMPLE LIX

To a stirred and cooled (below 10° C.) mixture of 5.04 parts of carbon disulfide, 2.06 parts of N,N'-methanetetraylbis[cyclohexamine] and 45 parts of tetrahydrofuran is added dropwise a solution of 3.7 parts of N-[1-(2-aminoethyl)-4-piperidinyl]-1-(4-fluorophenylmethyl)-1H-benzimidazol-2-amine in tetrahydrofuran. Upon completion, stirring is continued overnight while the mixture is allowed to reach room temperature. The reaction mixture is evaporated. The residue is purified by column-chromatography over silica gel using a mixture of trichloromethane and methanol (98:2 by volume) as eluent. The pure fractions are collected and the eluent is evaporated, yielding 4 parts (100%) of 1-(4-fluorophenylmethyl)-N-[1-(2-isothiocyanatoethyl)-4-piperidinyl]-1H-benzimidazol-2-amine as a residue.

A mixture of 2.1 parts of N-(4-fluorophenylmethyl)-1,2-benzenediamine, 4 parts of 1-(4-fluorophenylmethyl)-N-[1-(2-isothiocyanatoethyl)-4-piperidinyl]-1H-benzimidazol-2-amine and 90 parts of tetrahydrofuran is stirred and refluxed for 2 hours. The reaction mixture is evaporated, yielding 6 parts (100%) of N-{2-[(4-fluorophenylmethyl)amino]phenyl}-N'-[2-{4-[1-(4-fluorophenylmethyl)-1H-benzimidazol-2-ylamino]-1-piperidinyl}-ethyl]thiourea as a residue.

A mixture of 6 parts of N-{2-[(4-fluorophenylmethyl)amino]phenyl}-N'-[2-{4-[1-(4-fluorophenylmethyl)-1H-benzimidazol-2-ylamino]-1-piperidinyl}ethyl]thiourea, 3.2 parts of mercury (II) oxide, 0.1 parts of sulfur. and 90 parts of tetrahydrofuran is stirred and refluxed for 3 hours. The reaction mixture is filtered over Hyflo and the filtrate is evaporated. The residue is purified by column-chromatography over silica gel using a mixture of trichloromethane and methanol (98:2 by volume) as eluent. The pure fractions are collected and the eluent is evaporated. The residue is crystallized from a mixture of 2-propanone and 2,2'-oxybispropane, yielding 1.2 parts (20%) of 1-(4-fluorophenylmethyl)-N-[1-{2-[1-(4-fluorophenylmethyl)-1H-benzimidazol-2-ylamino]ethyl}-4-piperidinyl]-1H-benzimidazol-2-amine; mp. 196.9° C.

What is claimed is:

1. A chemical compound selected from the group consisting of a N-heterocyclyl-4-piperidinamine having the formula

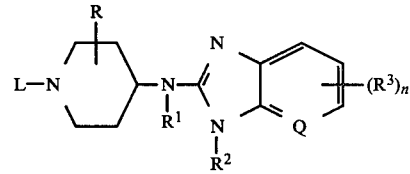

and the pharmaceutically acceptable acid addition salts thereof, wherein

R is a member selected from the group consisting of hydrogen and lower alkyl;

$R^1$ is a member selected from the group consisting of hydrogen, lower alkyl, cycloalkyl, aryllower alkyl and lower alkanoyl;

$R^2$ is a member from the group consisting of hydrogen, alkyl having from 1 to 10 carbon atoms, aryl, cycloalkyl and mono- and diaryl(lower alkyl);

$R^3$ is a member independently selected from the group consisting of, halo, lower alkyl, lower alkyloxy and trifluoromethyl;

n is an integer of from 0 to 2 inclusive;

Q is a member selected from the group consisting of CH and N; and

L is a member selected from the group consisting of lower alkyl, which is optionally substituted with up to 3 substituents each independently selected from the group consisting of halo, cyano, hydroxy, isothiocyanato, lower alkyloxy, aryl, aryloxy, arylthio, arylsulfonyl, amino; lower alkenyl; aryl-lower alkenyl; cycloalkyl, being optionally substituted with a cyano and/or or an aryl group; 1-(aryllower alkyl)-1H-benzimidazol-2-yl; and a radical of the formula Z-$C_mH_{2m}$-, wherein m is an integer of from 1 to 6 inclusive; and Z is a member selected from the group consisting of 4,5-dihydro-5-oxo-1H-tetrazol-1-yl, being optionally substituted in its 4-position by an aryl radical or a lower alkyl radical; 2,3-dihydro-1,4-benzodioxin-2-yl; 2,3-dihydro-1,4-benzodioxin-6-yl; 2,3-dihydro-2-oxo-1H-benzimidazol-1-yl; 2,3-dihydro-3-oxo-4H-benzoxazin-4-yl; (10,11-dihydro-5H-dibenzo[a,d]cyclohepten-5-ylidene)methyl; 4-morpholinyl; 1-piperidinyl; 1-pyrrolidinyl; a radical of the formula T-N($R^4$)-, wherein $R^4$ is a member selected from the group consisting of hydrogen, lower alkyl and aryllower alkyl; and T is a member selected from the group consisting of lower alkyl, aryl, aryllower alkyl, 1H-benzimidazol-2-yl; and a radical of the formula $$W-\overset{O}{\underset{\|}{C}}-(X)_s-,$$

wherein s is the integer 0 or 1;

X is a member selected from the group consisting of O and —N($R^5$)-, said $R^5$ being a member selected from the group consisting of hydrogen, lower alkyl, aryllower alkyl, lower alkanoyl and aroyl; and W is a member selected from the group consisting of lower alkyl, aryl, aryllower alkyl, amino, arylamino, mono- and di(lower alkyl)amino, mono- and di(aryllower alkyl)amino, 1-piperidinyl, 1-pyrrolidinyl and 4-morpholinyl;

where aryl as used in the foregoing definitions, is a member selected from the group consisting of phenyl, substituted phenyl, naphthalenyl, thienyl, halothienyl, (lower alkyl)thienyl, pyridinyl, mono- and di(lower alkyloxy)pyridinyl, furanyl and 1-(lower alkyl)pyrrolyl; wherein said substituted phenyl is phenyl having from 1 to 3 substituents each independently selected from the group consisting of halo, hydroxy, nitro, cyano, trifluoromethyl, lower alkyl, lower alkylthio, lower alkylsulfonyl, lower alkylsulfonyllower alkyl, phenyllower alkylsulfonyl, phenylsulfonyllower alkyl, amino, mono- and di-(lower alkyl)amino, lower alkanoyl, a radical of the formula $R^6$—$C_pH_{2p}$—O—, wherein p is an integer of from 1 to 6 inclusive; and $R^6$ is a member selected from the group consisting of hydrogen, amino, cyano, phenyl, aminocarbonyl, mono- and di(lower alkyl)aminocarbonyl, lower alkyloxycarbonyl, phenyllower alkyloxycarbonyl, 4-morpholinylcarbonyl, 1-piperidinylcarbonyl and 1-pyrrolidinylcarbonyl, and a radical of the formula $R^7$—O—, wherein $R^7$ is a member selected from the group consisting of alkanoyl, phenylcarbonyl, phenyllower alkylcarbonyl, lower alkyloxycarbonyl, phenyllower alkyloxycarbonyl, aminocarbonyl, phenylaminocarbonyl, mono- and di-(lower alkyl)aminocarbonyl wherein said phenyl in the definition of said $R^7$ may be optionally substituted with up to 3 substituents each independently selected from the group consisting of halo, cyano, nitro, lower alkyl and lower alkyloxy; and wherein said aroyl in the definition of said L represents arylcarbonyl wherein said aryl is as defined hereabove.

2. A chemical compound selected from the group consisting of 1-(4-fluorophenylmethyl)-N-{1-[2-(4-methoxyphenyl)ethyl]-4-piperidinyl}-1H-benzimidazol-2-amine and the pharmaceutically acceptable acid addition salts thereof.

3. A chemical compound selected from the group consisting of 4-[2-{4-[1-(4-fluorophenylmethyl)-1H-benzimidazol-2-ylamino]-1-piperidinyl}ethyl]phenol and the pharmaceutically acceptable acid addition salts thereof.

4. A chemical compound selected from the group consisting of {4-[2-{4-[1-(4-fluorophenylmethyl)-1H-benzimidazol-2-ylamino]-1-piperidinyl}ethyl]phenyl}-benzeneacetate and the pharmaceutically acceptable acid addition salts thereof.

5. A chemical compound selected from the group consisting of {4-[2-{4-[1-(4-fluorophenylmethyl)-1H-benzimidazol-2-ylamino]-1-piperidinyl}ethyl]phenoxy}acetonitrile and the pharmaceutically acceptable acid addition salts thereof.

6. An antihistaminic pharmaceutical composition comprising an inert carrier material and as an active ingredient an effective antihistaminic amount of a chemical compound selected from the group consisting of a N-heterocyclyl-4-piperidinamine having the formula (I)

and the pharmaceutically acceptable acid addition salts thereof, wherein

R is a member selected from the group consisting of hydrogen and lower alkyl;

$R^1$ is a member selected from the group consisting of hydrogen, lower alkyl, cycloalkyl, aryllower alkyl and lower alkanoyl;

$R^2$ is a member selected from the group consisting of hydrogen, alkyl having from 1 to 10 carbon atoms, aryl, cycloalkyl and mono- and diaryl(lower alkyl);

$R^3$ is a member independently selected from the group consisting of halo, lower alkyl, lower alkyloxy, trifluoromethyl;

n is an integer of from 0 to 2 inclusive;

Q is a member selected from the group consisting of CH and N; and

L is a member selected from the group consisting of lower alkyl, which is optionally substituted with up to 3 substituents each independently selected from the group consisting of halo, cyano, hydroxy, isothiocyanato, lower alkyloxy, aryl, aryloxy, arylthio, arylsulfonyl, amino; lower alkenyl; aryl-lower alkenyl; cycloalkyl, being optionally substituted with a cyano and/or an aryl group; 1-(aryllower alkyl)-1H-benzimidazol-2-yl; and a radical of the formula Z-$C_mH_{2m}$--, wherein m is an integer of from 1 to 6 inclusive; and Z is a member selected from the group consisting of 4,5-dihydro-5-oxo-1H-tetrazol-1-yl, being optionally substituted in its 4-position by an aryl radical or a lower alkyl radical; 2,3-dihydro-1,4-benzodioxin-2-yl; 2,3-dihydro-1,4-benzodioxin-6-yl; 2,3-dihydro-2-oxo-1H-benzimidazol-1-yl; 2,3-dihydro-3-oxo-4H-benzoxazin-4-yl; (10,11-dihydro-5H-dibenzo[a,d]cyclohepten-5-ylidene)methyl; 4-morpholinyl; 1-piperidinyl; 1-pyrrolidinyl; a radical of the formula T-N($R^4$)-, wherein $R^4$ is a member selected from the group consisting of hydrogen, lower alkyl and aryllower alkyl; and T is a member selected from the group consisting of lower alkyl, aryl, aryllower alkyl, 1H-benzimidazol-2yl; and a radical of the formula

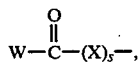

wherein s is the integer 0 or 1;

X is a member selected from the group consisting of O and -N($R^5$)-, said $R^5$ being a member selected from the group consisting of hydrogen, lower alkyl, aryllower alkyl, lower alkanoyl and aroyl; and W is a member selected from the group consisting of lower alkyl, aryl, aryllower alkyl, amino, arylamino, mono- and di(lower alkyl)amino, mono- and di(aryllower alkyl)amino, 1-piperidinyl, 1-pyrrolidinyl and 4-morpholinyl;

wherein aryl as used in the foregoing definitions, is a member selected from the group consisting of phenyl, substituted phenyl, naphthalenyl, thienyl, halothienyl, (lower alkyl)thienyl, pyridinyl, mono- and di(lower alkyloxy)pyridinyl, furanyl and 1-(lower alkyl)pyrrolyl; wherein said substituted phenyl is phenyl having from 1 to 3 substituents each independently selected from the group consisting of halo, hydroxy, nitro, cyano, trifluoromethyl, lower alkyl, lower alkylthio, lower alkylsulfonyl, lower alkylsulfonyllower alkyl, phenyllower alkylsulfonyl, phenylsulfonyllower alkyl, amino, mono- and di-(lower alkyl)amino, lower alkanoyl, a radical of the formula $R^6$—$C_pH_{2p}$—O—, wherein p is an integer of from 1 to 6 inclusive; and $R^6$ is a member selected from the group consisting of hydrogen, amino, cyano, phenyl, aminocarbonyl, mono- and di(lower alkyl)aminocarbonyl, lower alkyloxycarbonyl, phenyllower alkyloxycarbonyl, 4-morpholinylcarbonyl, 1-piperidinylcarbonyl and 1-pyrrolidinylcarbonyl, lower alkenyl; and a radical of the formula $R^7$-O-, wherein $R^7$ is a member selected from the group consisting of alkanoyl, phenylcarbonyl, phenyllower alkylcarbonyl, lower alkyloxycarbonyl, phenyllower alkyloxycarbonyl, aminocarbonyl, phenylaminocarbonyl, mono- and di-(lower alkyl)aminocarbonyl, wherein said phenyl in the definition of said $R^7$ may be optionally substituted with up to 3 substituents each independently selected from the group consisting of halo, cyano, nitro, lower alkyl and lower alkyloxy; and wherein said aroyl in the definition of said L represents arylcarbonyl wherein said aryl is as defined hereabove.

7. An antihistaminic pharmaceutical composition comprising an inert carrier material and as an active ingredient an effective antihistaminic amount of a chemical compound selected from the group consisting of 1-(4-fluorophenylmethyl)-N-{1-[2-(4-methoxyphenyl)ethyl]-4-piperidinyl}-1H-benzimidazol-2-amine and the pharmaceutically acceptable acid addition salts thereof.

8. An antihistaminic pharmaceutical composition comprising an inert carrier material and as an active ingredient an effective antihistaminic amount of a chemical compound selected from the group consisting of 4-[2-{4-[1-(4-fluorophenylmethyl)-1H-benzimidazol-2-ylamino]-1-piperidinyl}ethyl]phenol and the pharmaceutically acceptable acid addition salts thereof.

9. An antihistaminic pharmaceutical composition comprising an inert carrier material and as an active ingredient an effective antihistaminic amount of a chemical compound selected from the group consisting of {4-[2-{4-[1-(4-fluorophenylmethyl)-1H-benzimidazol-2-ylamino]-1-piperidinyl}ethyl]phenyl}benzeneacetate and the pharmaceutically acceptable acid addition salts thereof.

10. An antihistaminic pharmaceutical composition comprising an inert carrier material and as an active ingredient an effective antihistaminic amount of a chemical compound selected from the group consisting of {4-[2-{4-[1-(4-fluorophenylmethyl)-1H-benzimidazol-2-ylamino]-1-piperidinyl}ethyl]phenoxy}acetonitrile and the pharmaceutically acceptable acid addition salts thereof.

11. A method to prevent the release of histamine in warm-blooded animals, which comprises the systemic administration to said animals of an effective antihistaminic amount of a chemical compound selected from the group consisting of a N-heterocyclyl-4-piperidinamine having the formula

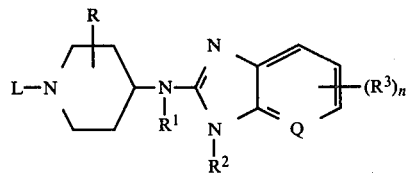

and the pharmaceutically acceptable acid addition salts thereof, wherein

R is a member selected from the group consisting of hydrogen and lower alkyl;

$R^1$ is a member selected from the group consisting of hydrogen, lower alkyl, cycloalkyl, aryllower alkyl and lower alkanoyl;

$R^2$ is a member selected from the group consisting of hydrogen, alkyl having from 1 to 10 carbon atoms, aryl, cycloalkyl and mono- and diaryl(lower alkyl);

$R^3$ is a member independently selected from the group consisting of halo, lower alkyl, lower alkyloxy, trifluoromethyl;

n is an integer of from 0 to 2 inclusive;

Q is a member selected from the group consisting of CH and N; and

L is a member selected from the group consisting of lower alkyl, which is optionally substituted with up to 3 substituents each independently selected from the group consisting of halo, cyano, hydroxy, isothiocyanato, lower alkyloxy, aryl, aryloxy, arylthio, arylsulfonyl, amino; lower alkenyl; aryllower alkenyl; cycloalkyl, being optionally substituted with a cyano and/or an aryl group; 1-(aryllower alkyl)-1H-benzimidazol-2-yl; and a radical of the formula Z-$C_mH_{2m}$-, wherein m is an integer of from 1 to 6 inclusive; and Z is a member selected from the group consisting of 4,5-dihydro-5-oxo-1H-tetrazol-1-yl, being optionally substituted in its 4-position by an aryl radical or a lower alkyl radical; 2,3-dihydro-1,4-benzodioxin-2-yl; 2,3-dihydro-1,4-benzodioxin-6-yl; 2,3-dihydro-2-oxo-1H-benzimidazol-1yl; 2,3-dihydro-3-oxo-4H-benzoxazin-4-yl; (10,11-dihydro-5H-dibenzo[a,d]cyclohepten-5-ylidene)methyl; 4-morpholinyl; 1-piperidinyl; 1-pyrrolidinyl; a radical of the formula T-N($R^4$)-, wherein $R^4$ is a member selected from the group consisting of hydrogen, lower alkyl and aryllower alkyl; and T is a member selected from the group consisting of lower alkyl, aryl, aryllower alkyl, 1H-benzimidazol-2-yl; and a radical of the formula

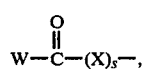

wherein s is the integer 0 or 1;

X is a member selected from the group consisting of O and -N($R^5$)—, said $R^5$ being a member selected from the group consisting of hydrogen, lower alkyl, aryllower alkyl, lower alkanoyl and aroyl; and W is a member selected from the group consisting of lower alkyl, aryl, aryllower alkyl, amino, arylamino, mono- and di(lower alkyl)amino, mono- and di(aryllower alkyl)amino, 1-piperidinyl, 1-pyrrolidinyl and 4-morpholinyl;

wherein aryl as used in the foregoing definitions, is a member selected from the group consisting of phenyl, substituted phenyl, naphthalenyl, thienyl, halothienyl, (lower alkyl)thienyl, pyridinyl, mono- and di(lower alkyloxy)pyridinyl, furanyl and 1-(lower alkyl)pyrrolyl; wherein said substituted phenyl is phenyl having from 1 to 3 substituents each independently selected from the group consisting of halo, hydroxy, nitro, cyano, trifluoromethyl, lower alkyl, lower alkylthio, lower alkylsulfonyl, lower alkylsulfonyllower alkyl, phenyllower alkylsulfonyl, phenylsulfonyllower alkyl, amino, mono- and di-(lower alkyl)amino, lower alkanoyl, a radical of the formula $R^6$—$C_pH_{2p}$-O—, wherein p is an integer of from 1 to 6 inclusive; and $R^6$ is a member selected from the group consisting of hydrogen, amino, cyano, phenyl, aminocarbonyl, mono- and di(lower alkyl)aminocarbonyl, lower alkyloxycarbonyl, phenyllower alkyloxycarbonyl, 4-morpholinylcarbonyl, 1-piperidinylcarbonyl and 1-pyrrolidinylcarbonyl, lower alkenyl; and a radical of the formula $R^7$-O—, wherein $R^7$ is a member selected from the group consisting of alkanoyl, phenylcarbonyl, phenyllower alkylcarbonyl, lower alkyloxycarbonyl, phenyllower alkyloxycarbonyl, aminocarbonyl, phenylaminocarbonyl, mono- and di(lower alkyl)aminocarbonyl, wherein said phenyl in the definition of said $R^7$ may be optionally substituted with up to 3 substituents each independently selected from the group consisting of halo, cyano, nitro, lower alkyl and lower alkyloxy; and wherein said aroyl in the definition of said L represents arylcarbonyl wherein said aryl is as defined hereabove.

12. A method to prevent the release of histamine is warm-blooded animals, which comprises the systemic administration to said animals of an effective antihistaminic amount of a chemical compound selected from the group consisting of 1-(4-fluorophenylmethyl)-N-{1-[2-(4-methoxyphenyl)ethyl]-4-piperidinyl}-1H-benzimidazol-2-amine and the pharmaceutically acceptable acid addition salts thereof.

13. A method to prevent the release of histamine in warm-blooded animals, which comprises the systemic administration to said animals of an effective antihistaminic amount of a chemical compound selected from the group consisting of 4-[2-{4-[1-(4-fluorophenylmethyl)-1H-benzimidazol-2-ylamino]-1-piperidinyl}-ethyl]phenol and the pharmaceutically acceptable acid addition salts thereof.

14. A method to prevent the release of histamine in warm-blooded animals, which comprises the systemic administration to said animals of an effective antihistaminic amount of a chemical compound selected from the group consisting of {4-[2-{4-[1-(4-fluorophenylmethyl)-1H-benzimidazol-2-ylamino]-1-piperidinyl}ethyl]-phenyl}benzeneacetate and the pharmaceutically acceptable acid addition salts thereof.

15. A method to prevent the release of histamine in warm-blooded animals, which comprises the systemic administration to said animals of an effective antihistaminic amount of a chemical compound selected from the group consisting of {4-[2-{4-[1-(4-fluorophenylmethyl)-1H-benzimidazol-2-ylamino]-1-piperidinyl}ethyl]-phenoxy}acetonitrile and the pharmaceutically acceptable acid addition salts thereof.

16. A chemical compound having the formula

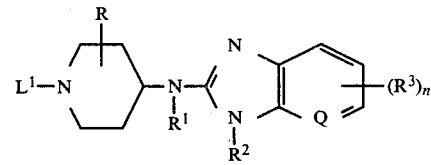

wherein:

$L^1$ is a member selected from the group consisting of hydrogen, lower alkyloxycarbonyl and phenylmethoxycarbonyl;

R is a member selected from the group consisting of hydrogen and lower alkyl;

$R^1$ is a member selected from the group consisting of hydrogen lower alkyl, cycloalkyl, aryllower alkyl and lower alkanoyl;

$R^2$ is a member selected from the group consisting of hydrogen, alkyl having from 1 to 10 carbon atoms, aryl, cycloalkyl and mono- and diaryl(lower alkyl);

R³ is a member independently selected from the group consisting of, halo, lower alkyl, lower alkyloxy, trifluoromethyl;

n is an integer of from 0 to 2 inclusive;

Q is a member selected from the group consisting of CH and N; and wherein aryl as used in the foregoing definitions, is a member selected from the group consisting of phenyl, substituted phenyl, naphthalenyl, thienyl, halothienyl, (lower alkyl)thienyl, pyridinyl, mono- and di(lower alkyloxy)pyridinyl, furanyl and 1-(lower alkyl)pyrrolyl; wherein said substitued phenyl is phenyl having from 1 to 3 substituents each independently selected from the group consisting of halo, hydroxy, nitro, cyano, trifluoromethyl, lower alkyl, lower alkylthio, lower alkylsulfonyl, lower alkylsulfonyllower alkyl, phenyllower alkylsulfonyl, phenylsulfonyllower alkyl, amino, mono- and di-(lower alkyl)amino, lower alkanoyl, a radical of the formula R⁶—$C_pH_{2p}$—O—, wherein p is an integer of from 1 to 6 inclusive; and R⁶ is a member selected from the group consisting of hydrogen, amino, cyano, phenyl, aminocarbonyl, mono- and di(lower alkyl)aminocarbonyl, lower alkyloxycarbonyl, phenyllower alkyloxycarbonyl, 4-morpholinylcarbonyl, 1-piperidinylcarbonyl and 1-pyrrolidinylcarbonyl, lower alkenyl; and a radical of the formula R⁷-O-, wherein R⁷ is a member selected from the group consisting of alkanoyl, phenylcarbonyl, phenyllower alkylcarbonyl, lower alkyloxycarbonyl, phenyllower alkyloxycarbonyl, aminocarbonyl, phenylaminocarbonyl, mono- and di(lower alkyl)aminocarbonyl and phenylcarbonyl, wherein said phenyl in the definition of said R⁷ may be optionally substituted with up to 3 substituents each independently selected from the group consisting of halo, cyano, nitro, lower alkyl and lower alkyloxy.

17. A chemical compound selected from the group consisting of a N-heterocyclyl-4-piperidinamine having the formula

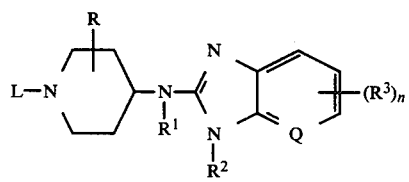

and the pharmaceutically acceptable acid addition salts thereof, wherein

R is a member selected from the group consisting of hydrogen and lower alkyl;

R¹ is a member selected from the group consisting of hydrogen, lower alkyl, cycloalkyl, aryllower alkyl and lower alkanoyl;

R² is a member selected from the group consisting of hydrogen, alkyl having from 1 to 10 carbon atoms, aryl, cycloalkyl and mono- and diaryl(lower alkyl);

R³ is a member independently selected from the group consisting of halo, lower alkyl, lower alkyloxy and trifluoromethyl;

n is an integer of from 0 to 2 inclusive; Q is a member selected from the group consisting of CH and N; and L is a member selected from the group consisting of lower alkyl, which is optionally substituted with up to 3 substituents each independently selected from the group consisting of halo, cyano, hydroxy, isothiocyanato, lower alkyloxy, aryl, aryloxy, arylthio, arylsulfonyl, amino; lower alkenyl; and aryllower alkenyl; wherein aryl as used in the foregoing definitions, is a member selected from the group consisting of phenyl, substituted phenyl, naphthalenyl, thienyl, halothienyl, (lower alkyl)thienyl, pyridinyl, mono- and di(lower alkyloxy)pyridinyl, furanyl and 1-(lower alkyl)pyrrolyl; wherein said substituted phenyl is phenyl having from 1 to 3 substituents each independently selected from the group consisting of halo, hydroxy, nitro, cyano, trifluoromethyl, lower alkyl, lower alkylthio, lower alkylsulfonyl, lower alkylsulfonyllower alkyl, phenyllower alkylsulfonyl, phenylsulfonyllower alkyl, amino, mono- and di-(lower alkyl)amino, lower alkanoyl, a radical of the formula R⁶—$C_pH_{2p}$—O—, wherein p is an integer of from 1 to 6 inclusive; and R⁶ is a member selected from the group consisting of hydrogen, amino, cyano, phenyl, aminocarbonyl, mono- and di(lower alkyl)aminocarbonyl, lower alkyloxycarbonyl, phenyllower alkyloxycarbonyl, 4-morpholinylcarbonyl, 1-piperidinylcarbonyl and 1-pyrrolidinylcarbonyl, and a radical of the formula R⁷—O—, wherein R⁷ is a member selected from the group consisting of alkanoyl, phenylcarbonyl, phenyllower alkylcarbonyl, lower alkyloxycarbonyl, phenyllower alkyloxycarbonyl, aminocarbonyl, phenylaminocarbonyl, mono- and di-(lower alkyl)aminocarbonyl, wherein said phenyl in the definition of said R⁷ may be optionally substituted with up to 3 substituents each independently selected from the group consisting of halo, cyano, nitro, lower alkyl and lower alkyloxy.

18. An antihistaminic pharmaceutical composition comprising an inert carrier material and as an active ingredient an effective antihistaminic amount of a chemical compound selected from the group consisting of a N-heterocyclyl-4-piperidinamine having the formula

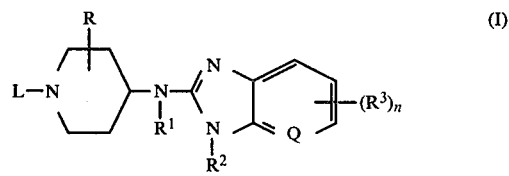

(I)

and the pharmaceutically acceptable acid addition salts thereof, wherein

R is a member selected from the group consisting of hydrogen and lower alkyl;

R¹ is a member selected from the group consisting of hydrogen, lower alkyl, cycloalkyl, aryllower alkyl and lower alkanoyl;

R² is a member selected from the group consisting of hydrogen, alkyl having from 1 to 10 carbon atoms, aryl, cycloalkyl and mono- and diaryl(lower alkyl);

R³ is a member independently selected from the group consisting of halo, lower alkyl, lower alkyloxy, trifluoromethyl;

n is an integer of from 0 to 2 inclusive;

Q is a member selected from the group consisting of CH and N; and L is a member selected from the group consisting of lower alkyl, which is optionally substituted with up to 3 substituents each independently selected from the group consisting of halo, cyano, hydroxy, isothiocyanato, lower alkyloxy, aryl, aryloxy, arylthio, arylsulfonyl, amino; lower alkenyl and aryllower alkenyl; wherein aryl as used in the foregoing definitions, is a member selected from the group consisting of phenyl, substituted phenyl, naphthalenyl, thienyl, halothienyl, (lower alkyl)thienyl, pyridinyl, mono- and di(lower alkyloxy)pyridinyl, furanyl and 1-(lower alkyl)pyrrolyl; wherein said substituted phenyl is phenyl having from 1 to 3 substituents each independently selected from the group consisting of halo, hydroxy, nitro, cyano, trifluoromethyl, lower alkyl, lower alkylthio, lower alkylsulfonyl, lower alkylsulfonyllower alkyl, phenyllower alkylsulfonyl, phenylsulfonyllower alkyl, amino, mono- and di-(lower alkyl)amino, lower alkanoyl, a radical of the formula $R^6\text{---}C_pH_{2p}\text{---}O\text{---}$, wherein p is an integer of from 1 to 6 inclusive; and $R^6$ is a member selected from the group consisting of hydrogen, amino, cyano, phenyl, aminocarbonyl, mono- and di(lower alkyl)aminocarbonyl, lower alkyloxycarbonyl, phenyllower alkyloxycarbonyl, 4-morpholinylcarbonyl, 1-piperidinylcarbonyl and 1-pyrrolidinylcarbonyl, lower alkenyl; and a radical of the formula $R^7\text{---}O\text{---}$, wherein $R^7$ is a member selected from the group consisting of alkanoyl, phenylcarbonyl, phenyllower alkylcarbonyl, lower alkyloxycarbonyl, phenyllower alkyloxycarbonyl, aminocarbonyl, phenylaminocarbonyl, mono- and di-(lower alkyl)aminocarbonyl, wherein said phenyl in the definition of said $R^7$ may be optionally substituted with up to 3 substituents each independently selected from the group consisting of halo, cyano, nitro, lower alkyl and lower alkyloxy.

19. A method to prevent the release of histamine in warm-blooded animals, which comprises the systemic administration to said animals of an effective antihistaminic amount of a chemical compound selected from the group consisting of a N-heterocyclyl-4-piperidinamine having the formula

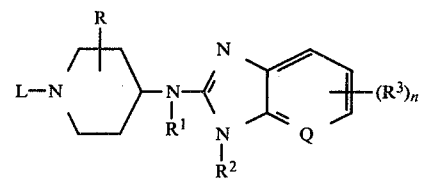

and the pharmaceutically acceptable acid addition salts thereof, wherein

R is a member selected from the group consisting of hydrogen and lower alkyl;

$R^1$ is a member selected from the group consisting of hydrogen, lower alkyl, cycloalkyl, aryllower alkyl and lower alkanoyl;

$R^2$ is a member selected from the group consisting of hydrogen, alkyl having from 1 to 10 carbon atoms, aryl, cycloalkyl and mono- and diaryl(lower alkyl);

$R^3$ is a member independently selected from the group consisting of halo, lower alkyl, lower alkyloxy, trifluoromethyl;

n is an integer of from 0 to 2 inclusive;

Q is a member selected from the group consisting of CH and N; and

L is a member selected from the group consisting of lower alkyl, which is optionally substituted with up to 3 substituents each independently selected from the group consisting of halo, cyano, hydroxy, isothiocyanato, lower alkyloxy, aryl, aryloxy, arylthio, arylsulfonyl, amino; lower alkenyl; aryllower alkenyl; wherein aryl as used in the foregoing definitions, is a member selected from the group consisting of phenyl, substituted phenyl, naphthalenyl, thienyl, halothienyl, (lower alkyl)thienyl, pyridinyl, mono- and di(lower alkyloxy)pyridinyl, furanyl and 1-(lower alkyl)pyrrolyl; wherein said substituted phenyl is phenyl having from 1 to 3 substituents each independently selected from the group consisting of halo, hydroxy, nitro, cyano, trifluoromethyl, lower alkyl, lower alkylthio, lower alkylsulfonyl, lower alkylsulfonyllower alkyl, phenyllower alkylsulfonyl, phenylsulfonyllower alkyl, amino, mono- and di-(lower alkyl)amino, lower alkanoyl, a radical of the formula $R^6\text{---}C_pH$ ................... $2p\text{---}O\text{---}$, wherein p is an integer of from 1 to 6 inclusive; and $R^6$ is a member selected from the group consisting of hydrogen, amino, cyano, phenyl, aminocarbonyl, mono- and di(lower alkyl)aminocarbonyl, lower alkyloxycarbonyl, phenyllower alkyloxycarbonyl, 4-morpholinylcarbonyl, 1-piperidinylcarbonyl and 1-pyrrolidinylcarbonyl, lower alkenyl; and a radical of the formula $R^7\text{---}O\text{---}$, wherein $R^7$ is a member selected from the group consisting of alkanoyl, phenylcarbonyl, phenyllower alkylcarbonyl, lower alkyloxycarbonyl, phenyllower alkyloxycarbonyl, aminocarbonyl, phenylaminocarbonyl, mono- and di-(lower alkyl)aminocarbonyl, wherein said phenyl in the definition of said $R^7$ may be optionally substituted with up to 3 substituents each independently selected from the group consisting of halo, cyano, nitro, lower alkyl and lower alkyloxy.

* * * * *

UNITED STATES PATENT AND TRADEMARK OFFICE

CERTIFICATE EXTENDING PATENT TERM
UNDER 35 U.S.C. 156

Patent No.    : 4,219,559

Dated         : August 26, 1980

Inventor(s)   : FRANS JANSSENS ET AL

Patent Owner  : JANSSEN PHARMACEUTICA N.V.

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156 (b).

I have caused the seal of the Patent and Trademark Office to be affixed this 11th day of December 1989.

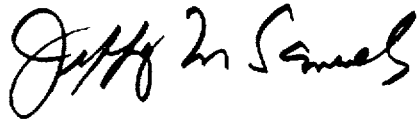

Jeffrey M. Samuels
Acting Commissioner of
  Patents and Trademarks